(12) United States Patent
Wei et al.

(10) Patent No.: US 9,358,113 B2
(45) Date of Patent: *Jun. 7, 2016

(54) DELIVERY SYSTEM

(75) Inventors: Guobao Wei, Eatontown, NJ (US);
Keyvan Behnam, Red Bank, NJ (US);
Nanette Forsyth, Bayville, NJ (US);
John Winterbottom, Howell, NJ (US);
James Beisser, Union Beach, NJ (US);
Todd M. Boyce, Matawan, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 715 days.

This patent is subject to a terminal disclaimer.

(21) Appl. No.: 12/171,125

(22) Filed: Jul. 10, 2008

(65) Prior Publication Data
US 2009/0192474 A1 Jul. 30, 2009

Related U.S. Application Data

(60) Provisional application No. 60/948,866, filed on Jul. 10, 2007, provisional application No. 61/040,531, filed on Mar. 28, 2008, provisional application No. 61/040,537, filed on Mar. 28, 2008.

(51) Int. Cl.
*A61F 2/28* (2006.01)
*A61B 17/70* (2006.01)
(Continued)

(52) U.S. Cl.
CPC .......... *A61F 2/2846* (2013.01); *A61B 17/7097* (2013.01); *A61F 2/28* (2013.01); *A61F 2/0095* (2013.01); *A61F 2/4455* (2013.01); *A61F 2/4601* (2013.01); *A61F 2002/285* (2013.01); *A61F 2002/2817* (2013.01); *A61F 2002/2835* (2013.01); *A61F 2002/2839* (2013.01)

(58) Field of Classification Search
CPC ............... A61B 17/7097; A61B 17/68; A61B 17/7022; A61B 17/7059; A61B 17/8085; A61F 2002/2817; A61F 2002/2835; A61F 2/0095; A61F 2/28; A61F 2/4455; A61F 2/4601; A61F 2002/2878; A61F 2002/30576; A61F 2002/30581; A61F 2002/30622; A61F 2002/3068; A61F 2002/30971; A61F 2250/0068; A61F 2/2846; A61F 2/3099
USPC .............. 604/890.1, 285; 514/2, 12; 424/549, 424/93.7

See application file for complete search history.

(56) References Cited

U.S. PATENT DOCUMENTS 4,172,128 A 10/1979 Thiele et al.
4,294,753 A 10/1981 Urist
(Continued)

FOREIGN PATENT DOCUMENTS

DE 2 253 086 9/1974
DE 693 24 117 T2 6/1994
(Continued)

OTHER PUBLICATIONS

Aspenberg P. et al., "Bone morphogenetic protein induces bone in the squirrel monkey, but bone matrix does not", *Acta Orthop Scand.* 63(6): 619-22 (Dec. 1992).
(Continued)

*Primary Examiner* — Imani Hayman
(74) *Attorney, Agent, or Firm* — Sorell Lenna & Schmidt LLP

(57) ABSTRACT

A covering for delivering a substance or material to a surgical site is provided. The covering, with substance provided therein, may be referred to as a delivery system. Generally, the covering may be a single or multi-compartment structure capable of at least partially retaining a substance provided therein until the covering is placed at a surgical site. Upon placement, the covering may facilitate transfer of the substance or surrounding materials. For example, the substance may be released (actively or passively) to the surgical site. The covering may participate in, control, or otherwise adjust, the release of the substance.

45 Claims, 13 Drawing Sheets

(51) Int. Cl.
  *A61F 2/00* (2006.01)
  *A61F 2/44* (2006.01)
  *A61F 2/46* (2006.01)

(56) References Cited

U.S. PATENT DOCUMENTS

| | | |
|---|---|---|
| 4,394,370 A | 7/1983 | Jefferies |
| 4,430,760 A | 2/1984 | Smestad |
| 4,440,370 A | 4/1984 | Rood |
| 4,440,750 A | 4/1984 | Glowacki et al. |
| 4,455,256 A | 6/1984 | Urist |
| 4,472,840 A | 9/1984 | Jefferies |
| 4,485,097 A | 11/1984 | Bell |
| 4,563,350 A | 1/1986 | Nathan et al. |
| 4,619,989 A | 10/1986 | Urist |
| 4,657,548 A | 4/1987 | Nichols |
| 4,678,470 A | 7/1987 | Nashef et al. |
| 4,743,259 A | 5/1988 | Bolander et al. |
| 4,755,184 A | 7/1988 | Silverberg |
| 4,761,471 A | 8/1988 | Urist |
| 4,774,228 A | 9/1988 | Seyedin et al. |
| 4,774,322 A | 9/1988 | Seyedin et al. |
| 4,787,906 A | 11/1988 | Haris |
| 4,789,663 A | 12/1988 | Wallace et al. |
| 4,789,732 A | 12/1988 | Urist |
| 4,795,804 A | 1/1989 | Urist |
| 4,804,744 A | 2/1989 | Sen |
| 4,810,691 A | 3/1989 | Seyedin et al. |
| 4,843,063 A | 6/1989 | Seyedin et al. |
| 4,902,296 A | 2/1990 | Bolander et al. |
| 5,041,138 A | 8/1991 | Vacanti et al. |
| 5,073,373 A | 12/1991 | O'Leary |
| 5,106,748 A | 4/1992 | Wozney et al. |
| 5,166,187 A | 11/1992 | Collombel et al. |
| 5,211,664 A | 5/1993 | Tepic et al. |
| 5,236,456 A | 8/1993 | O'Leary et al. |
| 5,266,683 A | 11/1993 | Oppermann et al. |
| 5,270,300 A | 12/1993 | Hunziker |
| 5,284,655 A | 2/1994 | Bogdansky et al. |
| 5,290,558 A | 3/1994 | O'Leary et al. |
| 5,290,763 A | 3/1994 | Poser et al. |
| 5,314,476 A | 5/1994 | Prewett et al. |
| 5,336,264 A | 8/1994 | Constanz et al. |
| 5,354,557 A | 10/1994 | Oppermann et al. |
| 5,378,469 A | 1/1995 | Kemp et al. |
| 5,385,887 A | 1/1995 | Yim et al. |
| 5,405,390 A | 4/1995 | O'Leary et al. |
| 5,490,962 A | 2/1996 | Cima et al. |
| 5,501,706 A | 3/1996 | Arenberg |
| 5,507,813 A | 4/1996 | Dowd et al. |
| 5,518,680 A | 5/1996 | Cima et al. |
| 5,531,735 A | 7/1996 | Thompson |
| 5,563,124 A | 10/1996 | Damien et al. |
| 5,571,189 A | 11/1996 | Kuslich |
| 5,607,269 A | 3/1997 | Dowd et al. |
| 5,618,339 A | 4/1997 | Ito |
| 5,658,882 A | 8/1997 | Celeste et al. |
| 5,723,012 A | 3/1998 | Fages et al. |
| 5,725,579 A | 3/1998 | Fages et al. |
| 5,776,193 A | 7/1998 | Kwan et al. |
| 5,788,959 A | 8/1998 | Singh |
| 5,807,437 A | 9/1998 | Sachs et al. |
| 5,830,493 A | 11/1998 | Yokota et al. |
| 5,846,484 A | 12/1998 | Scarborough et al. |
| 5,877,005 A | 3/1999 | Castor et al. |
| 5,894,070 A | 4/1999 | Hansson et al. |
| 5,899,939 A | 5/1999 | Boyce et al. |
| 5,902,562 A | 5/1999 | Lagasse et al. |
| 6,007,580 A | 12/1999 | Lehto et al. |
| 6,018,095 A | 1/2000 | Lerch et al. |
| 6,030,635 A | 2/2000 | Gertzman et al. |
| 6,117,646 A | 9/2000 | Qvist et al. |
| 6,120,558 A | 9/2000 | Poddevin et al. |
| 6,124,273 A | 9/2000 | Drohan et al. |
| 6,143,030 A | 11/2000 | Schroder |
| 6,149,864 A | 11/2000 | Dillow et al. |
| 6,162,258 A | 12/2000 | Scarborough et al. |
| 6,180,606 B1 | 1/2001 | Chen et al. |
| 6,197,325 B1 | 3/2001 | MacPhee et al. |
| 6,217,614 B1 | 4/2001 | Fages et al. |
| 6,245,537 B1 | 6/2001 | Williams et al. |
| 6,294,041 B1 | 9/2001 | Boyce et al. |
| 6,294,187 B1 | 9/2001 | Boyce et al. |
| 6,311,690 B1 | 11/2001 | Jefferies |
| 6,326,018 B1 | 12/2001 | Gertzman et al. |
| 6,352,667 B1 | 3/2002 | English |
| 6,372,257 B1 | 4/2002 | Marchosky |
| 6,387,391 B1 | 5/2002 | Shikinami et al. |
| 6,436,138 B1 | 8/2002 | Dowd et al. |
| 6,440,444 B2 | 8/2002 | Boyce et al. |
| 6,465,168 B1 | 10/2002 | Castor et al. |
| 6,468,543 B1 | 10/2002 | Gilbertson et al. |
| 6,478,825 B1 | 11/2002 | Winterbottom et al. |
| 6,592,886 B1 | 7/2003 | Zimmermann |
| 6,595,998 B2 | 7/2003 | Johnson et al. |
| 6,599,515 B1 | 7/2003 | Delmotte |
| 6,616,698 B2 | 9/2003 | Scarborough |
| 6,618,698 B1 | 9/2003 | Beausoleil et al. |
| 6,623,749 B2 | 9/2003 | Williams et al. |
| 6,648,919 B2 | 11/2003 | Ferree |
| 6,696,073 B2 | 2/2004 | Boyce et al. |
| RE38,522 E | 5/2004 | Gertzman et al. |
| 6,740,093 B2 | 5/2004 | Hochschuler et al. |
| 6,752,831 B2 | 6/2004 | Sybert et al. |
| 6,783,546 B2 | 8/2004 | Zucherman |
| 6,843,807 B1 | 1/2005 | Boyce et al. |
| 6,884,428 B2 | 4/2005 | Binette et al. |
| 6,884,778 B2 | 4/2005 | Jo et al. |
| 6,911,212 B2 | 6/2005 | Gertzman et al. |
| 6,953,594 B2 | 10/2005 | Lee et al. |
| 6,969,404 B2 | 11/2005 | Ferree |
| 6,989,029 B2 | 1/2006 | Bonutti |
| 7,001,390 B2 | 2/2006 | Gebhardt et al. |
| 7,008,591 B2 | 3/2006 | Kafesjian et al. |
| 7,019,192 B2 | 3/2006 | Gertzman et al. |
| 7,025,771 B2 | 4/2006 | Kuslich et al. |
| 7,045,141 B2 | 5/2006 | Merboth et al. |
| 7,060,287 B1 | 6/2006 | Hubbard et al. |
| 7,108,832 B2 | 9/2006 | Christensen et al. |
| 7,163,691 B2 | 1/2007 | Knaack et al. |
| 7,179,299 B2 | 2/2007 | Edwards et al. |
| 7,208,015 B2 | 4/2007 | Pointillart et al. |
| 7,220,282 B2 | 5/2007 | Kuslich |
| 7,226,481 B2 | 6/2007 | Kuslich |
| 7,241,303 B2 | 7/2007 | Reiss et al. |
| 7,261,720 B2 | 8/2007 | Stevens et al. |
| 2001/0031254 A1 | 10/2001 | Bianchi et al. |
| 2001/0043258 A1 | 11/2001 | Ohki |
| 2002/0058947 A1 | 5/2002 | Hochschuler et al. |
| 2002/0068974 A1 | 6/2002 | Kuslich et al. |
| 2002/0077701 A1 | 6/2002 | Kuslich |
| 2002/0133166 A1 | 9/2002 | McKay et al. |
| 2002/0197297 A1 | 12/2002 | Risbud et al. |
| 2003/0008328 A1 | 1/2003 | Wironen et al. |
| 2003/0039676 A1 | 2/2003 | Boyce et al. |
| 2003/0044445 A1 | 3/2003 | Kay et al. |
| 2003/0065392 A1 | 4/2003 | Fan et al. |
| 2003/0072677 A1 | 4/2003 | Kafesjian et al. |
| 2003/0143258 A1 | 7/2003 | Knaack et al. |
| 2003/0152548 A1 | 8/2003 | Mikos et al. |
| 2003/0194708 A1 | 10/2003 | Binnerts et al. |
| 2004/0023387 A1 | 2/2004 | Morris et al. |
| 2004/0024457 A1 | 2/2004 | Boyce et al. |
| 2004/0059364 A1 | 3/2004 | Gaskins et al. |
| 2004/0072322 A1 | 4/2004 | Thorne |
| 2004/0146543 A1 | 7/2004 | Shimp et al. |
| 2004/0220615 A1 | 11/2004 | Lin et al. |
| 2004/0249464 A1 | 12/2004 | Bindseil et al. |
| 2004/0249471 A1* | 12/2004 | Bindseil et al. ............ 623/23.51 |
| 2005/0008620 A1 | 1/2005 | Shimp et al. |
| 2005/0008672 A1 | 1/2005 | Winterbottom et al. |
| 2005/0020506 A1 | 1/2005 | Drapeau et al. |
| 2005/0027033 A1 | 2/2005 | Knaack et al. |
| 2005/0037978 A1 | 2/2005 | Damien |

(56) References Cited

U.S. PATENT DOCUMENTS

| | | | |
|---|---|---|---|
| 2005/0131417 A1 | 6/2005 | Ahern et al. | |
| 2005/0244450 A1 | 11/2005 | Reddi | |
| 2005/0244457 A1 | 11/2005 | Reddi | |
| 2005/0251267 A1 | 11/2005 | Winterbottom et al. | |
| 2005/0283255 A1 | 12/2005 | Geremakis et al. | |
| 2006/0129241 A1* | 6/2006 | Boyer et al. | 623/17.15 |
| 2006/0216321 A1 | 9/2006 | Lyu et al. | |
| 2006/0216323 A1 | 9/2006 | Knaack et al. | |
| 2006/0287732 A1 | 12/2006 | Pezeshkian | |
| 2007/0073401 A1 | 3/2007 | Pointillart et al. | |
| 2007/0093896 A1 | 4/2007 | Malinin | |
| 2007/0098756 A1 | 5/2007 | Behnam | |
| 2007/0110820 A1 | 5/2007 | Behnam | |
| 2007/0118222 A1 | 5/2007 | Lang | |
| 2007/0125700 A1 | 6/2007 | Ding et al. | |
| 2007/0142916 A1 | 6/2007 | Olson et al. | |
| 2007/0154563 A1 | 7/2007 | Behnam et al. | |
| 2007/0162132 A1 | 7/2007 | Messerli | |
| 2007/0178158 A1 | 8/2007 | Knaack et al. | |
| 2007/0231788 A1 | 10/2007 | Behnam et al. | |
| 2008/0027546 A1 | 1/2008 | Semler et al. | |
| 2008/0069852 A1 | 3/2008 | Shimp et al. | |
| 2008/0091270 A1 | 4/2008 | Miller et al. | |
| 2008/0260794 A1 | 10/2008 | Lauritzen et al. | |
| 2009/0087471 A1 | 4/2009 | Shimp et al. | |
| 2009/0130173 A1 | 5/2009 | Behnam et al. | |
| 2009/0155378 A1 | 6/2009 | Behnam et al. | |
| 2009/0157087 A1 | 6/2009 | Wei et al. | |
| 2009/0192474 A1 | 7/2009 | Wei et al. | |
| 2009/0220605 A1 | 9/2009 | Wei et al. | |

FOREIGN PATENT DOCUMENTS

| | | |
|---|---|---|
| EP | 0 082 621 A1 | 6/1983 |
| EP | 0 212 474 | 3/1987 |
| EP | 0 309 241 | 3/1989 |
| EP | 0 148 155 | 4/1989 |
| EP | 0 332 826 A1 | 9/1989 |
| EP | 0 440 991 | 8/1991 |
| EP | 0 567 391 A | 10/1993 |
| EP | 0 603 920 A1 | 6/1994 |
| EP | 0 621 020 A1 | 10/1994 |
| EP | 0781564 A2 | 7/1997 |
| JP | 01/179689 | 7/1989 |
| WO | WO 88/00205 | 1/1988 |
| WO | WO 88/01517 | 3/1988 |
| WO | WO 90/03733 | 4/1990 |
| WO | WO 94/21298 | 9/1994 |
| WO | WO 95/31948 | 11/1995 |
| WO | WO 96/39170 | 12/1996 |
| WO | WO 00/13615 | 3/2000 |
| WO | WO 00/45870 | 8/2000 |
| WO | WO 00/47736 | 8/2000 |
| WO | WO 01/28461 A2 | 4/2001 |
| WO | WO 01/70136 A2 | 9/2001 |
| WO | WO 01/79342 A2 | 10/2001 |
| WO | WO 02/069818 A2 | 9/2002 |
| WO | WO 03/025271 A1 | 3/2003 |
| WO | WO 03/030956 A3 | 4/2003 |
| WO | WO 2004/073563 A2 | 9/2004 |
| WO | WO 2005/065396 A2 | 7/2005 |
| WO | WO 2005/072656 A1 | 8/2005 |
| WO | WO 2005/081699 A2 | 9/2005 |
| WO | WO 2006/076712 | 7/2006 |
| WO | WO 2007/053850 | 5/2007 |
| WO | WO 2007/133451 | 11/2007 |

OTHER PUBLICATIONS

Blumenthal et al. "The use of collagen membrane barriers in conjunction with combined demineralized bone-collagen gel implants in human infrabony defects," *J. Periodontal* 61(6): 319-327 (Jun. 1990).

Bolander et al.,"The Use of Demineralized Bone Matrix in the Repair of Segmental Defects", *The Journal of Bone and Joint Surgery*, 68-A (8): 1264-1273.

Bravo, D.A. et al., "Accurate and Efficient Cleavage of the Human Insulin Proreceptor by the Human Proprotein-Processing Protease Furin," *Journal Biol Chem.* 269: 25830-25873 (1994).

Cameron, A. et al., "Polyarginines are potent inhibitors," *J. Biol. Chem.* 275: 36741-36749 (2000).

Canalis et al., "Bone morphogenetic proteins, their antagonists, and the skeleton," *Endocrine Rev.* 24(2): 218-235 (2003).

Canalis et al., "Stimulation of DNA and Collagen Synthesis by Autologous Growth Factor in Cultured Fetal Rat Calvaria," *Science*, 210:1021-1023 (1980).

Caplanis et al., "Effect of allogenic freeze-dried demineralized bone matrix on guided tissue regeneration in dogs," *J. Periodontal*, 851-856 (Aug. 1998).

Constantino, et al. "Bone Healing and Bone Substitutes," *Facial Plastic Surgery* 18(1): pp. 14-26 (2002).

Crowe et al., "Inhibition of Enzymatic Digestion of Amylose by Free Fatty Acids in Vitro Contributes to Resistant Starch Formation", *J. Nutr.*, 130(8): 2006-2008 (2000).

Cui et al., "The activity and signaling range of mature BMP-4 is regulated by sequential cleavage at two sites within the prodomain of the precursor," *Genes and Development*, 15:2797-2802 (2001).

Cui et al., "BMP-4 is proteolytically activated by furin and/or PC6 during vertebrae embryonic development," *The Embo Journal*, 17(16):4735-4743 (1998).

Deatherage et al., "Packaging and Delivery of Bone Induction Factors in a Collagenous Implant," *Collagen Rel. Res.* 7:225-231 (1987).

Driessens et al., "Calcium Phosphate Bone Cements," Universitat Politecnica de Catalunya, Barcelona, Spain, 31: 855-77.

Dubois et al., "Evidence that Furin Is an Authentic Transforming Growth Facto-B-1-Converting Enxyme," *American Journal of Pathology*, 158(1):305-316 (2001).

Edwards et al., "Osteoinduction of Human Demineralized Bone: Characterization in a Rat Model," *Clinical Orthopaedics & Rel. Res.*, 357: 219-228 (Dec. 1998).

Ueland et al., *J. Clin. Endocrinol. & Metab.*, 84(1): 123-127 (1999).

Urist. "Bone: Formation by Autoinduction," *Science*, 150(698): pp. 893-899 (1965).

Urist. "The Bone Induction Principle," *Clin. Ortho. Rel. Res.*, 55: 243-283 (1967).

Urist et al., "Bone morphogenesis in Implants of Insoluble Bone Gelatin," *Proc. Natl. Acad. Sci.*, , 70(12): 3511-5 (Dec. 1973).

Urist et al., .,"Preservation and biodegradation of the morphogenetic property of bone matrix," *J. Theor. Biol.* 38: 155-67 (1973).

Urist et al., "Observations implicating an extracellular enzymic mechanism of control of bone morphogenesis," *J. Histochem & Cytochem*, 22(2): 88-103 (1974).

Urist et al., "A Chemosterilized Antigen-Extracted Autodigested Alloimplant for Bone Banks," *Arch Surg.* vol. 110: 416-428 (Apr. 1975).

Urist et al., "Cartilage Tissue Differentiation from Mesenchymal Cells Derived from Mature Muscle in Tissue Culture", *In Vitro*, 14(8): 697-706 (1978).

Urist et al. "Intertransverse Process Fusion with the Aid of Chemosterilized Autolyzed Antigen-Extracted Allogeneic (AAA) Bone," *Clin. Ortho. and Related Research*, 154: 97-113 (1981).

Urist et al., "Human Bone Morphogenetic Protein (hBMP)," *Proc. Soc. Exp. Biol.* 173:194-199 (1983).

Urist et al., "Purification of bovine bone morphogenetic protein by hydroxyapatite chromatography," *Prop. Natl. Acad. Sci.* 81:371-375 (1984).

Van den Berg et al., "Tissue Engineering, Cells, Scaffolds, and Growth Factors," *Clin. Orthopaedics and Related Res.*, 391S: S244-S250 (2001).

Van den Ouweland, A.M.W. et al., "Structural homology between the human *fur* gene product and the subtilisin-like protease encoded by yeast *KEX2*," *Nucl. Acid Res.* 18(3): 664 (1990).

Wang et al., "Purification and characterization of other distinct bone-inducing factors," *Proc. Nat. Acad. Sci.* 85:9484-9488 (1988).

Wang et al., "Recombinant human bone morphogenetic protein induces bone formation," *Proc. Nat. Acad. Sci.* 87:2220-2224 (1990).

White et al., "Effective terminal sterilization using supercritical carbon dioxide," *Journal of Biotechnology*, 123: 504-515 (2006).

(56) References Cited

OTHER PUBLICATIONS

Whiteman et al., "Demineralized Bone Powder," *J. Hand. Surg.*, 18B(4): 487-90 (1993).
Whittaker et al., "Matrix Metalloproteinases and Their Inhibitors—Current Status and Future Challenges," *Celltransmissions*, 17(1): 3-14.
International Search Report dated Oct. 22, 2008.
Landesman, Richard et al., "In Vivo Analysis of the Half-Life of the Osteoinductive Potential of Demineralized Bone Matrix Using Diffusion Chambers", *Calcif. Tissue Int.*, vol. 45, No. 6 1989, 348-353.
Laursen, Malene et al., "Optimal Handling of freshcancellous bone graft—Different peroperative storing techniques evaluated by in vitro osteobalst-like cell metabolism", *Acta Orthop Scand.*, vol. 74, No. 4 2003, 491.
Aspenberg et al., "Monkey Bone Matrix Induces Bone Formation in the Athymic Rat, but Not in Adult Monkeys," *J. of Orthop. Res.* 9:20-25 1991).
Elliott, J.C., "Structure and Chemistry of the Apatites and Other Calcium Orthophosphates", Elsevier Science B.V., Amsterdam (1994).
Enlow, Donald H., "Principles of Bone Remodeling: An Account of Post-natal Growth and remodeling Processes in Long Bones and the Mandible," Charles C. Thomas, Springfield, Ill., (1963).
Farley et al., "Human Skeletal Growth Factor: Characterization of the Mitogenic Effect on Bone Cells in Vitro," *Biochem*, 21:3508-3513 (1982).
Flemmig, et al. "Long-Term Maintenance of Alveolar Bone Gain After Implantation of Autolyzed, Antigen-Extracted, Allogenic Bone in Periodontal Intraosseous Defects," *J. Periodontal*, 69(1): 47-53 (Jan. 1998).
Fujishiro, et al. "Histological evaluation of an impacted bone graft substitute composed of a combination of mineralized and demineralized allograft in a sheep vertebral bone defect," *Journal of Biomedical Materials Research Part A*, 538-544 (Aug. 4, 2006).
Gamradt, et al. "Bone Graft for Revision Hip Arthroplasty", *Clin. Ortho. and Related Research*, 417: 183-194 (2003).
Gepstein et al. "Bridging Large Defects in Bone by Demineralized Bone Matrix in the Form of a Powder," *The Journal of Bone and Joint Surgery*, 69A(7): 984-991 (1987).
Glowacki, "Cellular Reactions to Bone-Derived Material," *Clin. Ortho. and Related Research*, 324: 47-54 (1996).
Glowacki et al., "Fate of Mineralized and Demineralized Osseous Implants in Cranial Defects," *Calcif. Tissue Int.*, 33: 71-76 (1981).
Glowacki et al., "Demineralized bone implants," *Symposium on Horizons in Plastic Surgery*, 12(2): 233-41 (1985).
Han B., et al., "Quantitive and sensitive in vitro assay for osteoinductive activity of demineralized bone matrix," *J. Orthop. Res.* 21(4): 648-54 (Jul. 2003).
Han, C. et al. "Autolysed Antigen-Extracted Allogeneic Boen for Repair of Diaphyseal Boen Defects in Rabbits," *Yonsei Medical Journal*, 31(3): 251-257 (1990).
Hollinger, et al. "A comparison of four particulate bone derivatives," *Clin. Ortho. and Related Research*, 267: 255-263 (Jun. 1991).
Hunziker et al., "Repair of Partial Thickness Defects in Articulate Cartilage: Cell Recruitment From the Synovial Membrane", *Journal Bone Joint Surg.*, 78-A: 721-733 (1996).
Iwata et al. "Chemosterilized Autolyzed Antigen-Extracted Allogeneic (AAA) Bone Matrix Gelatin for Repair of Defects from Excision of Benign Bone Tumors," *Clin. Ortho and Related Research*, 154: 150-155 (1981).
Jain et al., "Anchoring of phospholipase $A_2$: the effect of anions and deuterated water, and the role of N-terminus region," *Biochem. Et Biophys. Acta*, 860: 448-461 (1986).
Janovec, et al. "Autolyzed Antigen-Extracted Allogeneic Bone for Bridging Segmented Diaphyseal Bone Defects in Rabbits," *Clin. Ortho. and Related Research*, 229: 249-256 (Apr. 1988).
Jean et al., "Alpha 1-Antitrypsin Portland, a bioengineered serpin highly selective for furin: Application as an antipathogenic agent", *Proc. Natl. Acad. Sci.*, USA 95: 7293-7298 (1998).

Johnson et al. "Human Bone Mortphogenetic Protein Allografting for Reconstruction of Femoral Nonunion," *Clin. Ortho. and Related Research*, 371: 61-74 (2000).
Johnson et al. "Preliminary explorations of reconstructive surgery with implants of autolyzed antigen-extracted allogeneic (AAA) bone supercharged with bone morphogenetic protein (BMP)," *Bone Grafts, Derivatives and Substitutes*, published by Butterworth-Heinemann, Oxford, pp. 363-376 (1994).
Johnson et al. "Resistant Nonunions and Partial or Complete Segmental Defects of Long Bones," *Clin. Ortho. and Related Research*, 277: 229-237 (Apr. 1992).
Kaban et al., "Treatment of Jaw Defects with Demineralized Bone Implants", *Journal of Oral and Maxillofacial Surgery*, pp. 623-626 (Jun. 6, 1989).
Kasten et al., "Comparison of Human Bone Marrow Stromal Cells Seeded on Calcium-Deficient Hydroxyapatite, Betatricalcium Phosphate and Demineralized Bone Matrix", *Biomaterials*, 24(15):2593-603 (2003).
Katz, "The Biology of Heavy Water," *Scientific American*, 106-116 (1960).
Kawai et al., *Clin. Orthopaedics and Related Res.*, 233: 262-267 (1988).
Krysan, D.J., et al., "Quantitative Characterization of Furin Specificity", *Journal Biol. Chem.* 274, pp. 23229-23234 (1999).
Kubler et al. "Allogenic Bone & Cartilage Morphogenesis," *J. Craniomaxillofac. Surg.*, 19(7): 283-288 (1991).
Kubler et al. "Osteoinductive, morphologic, and biomechanical properties of autolyzed, antigen-extracted, allogeneic human bone," *J. Oral Maxillofac Surg*, 51: 1346-1357 (1993).
Kubler et al. "Repair of human skull defects using osteoinductive bone alloimplants," *J. of Cranio Maxillofac. Surg.* 23: 337-346 (1995).
Lee et al., *Nature*, 424: 389 (2003).
Lewandrowski et al., "Flexural Rigidity in Partially Demineralized Diaphyseal Bone Grafts", *Clin, Ortho. Rel. Res.*, 317: 254-262 (1995).
Lewandrowski et al. "Improved Osteoinduction of Cortical Bone Allografts: A Study of the Effects of Laser Perforation and Partial Demineralization" *J. Orthop. Res.* vol. 15(5): 748-756 (1997).
Lewandrowski et al. "Kinetics of cortical bone demineralization: Controlled demineralization—a new method for modifying cortical bone allografts", *Journal of Biomedical Materials Research*, vol. 31: 365-372 (1996).
Lewandrowski et al. "Mechanical Properties of Perforated and Partially Demineralized Bone Grafts," *Clin. Ortho. and Related Research*, 353: 238-246 (1998).
Lewandrowski et al., "An Electron Microscopic Study on the Process of Acid Demineralization of Cortical Bone," *Calcified Tissue Int.* 61:294-297 (1997).
Lieberman, et al. "Treatment of Osteonecrosis of the Femoral Head with Core Decompression and Human Bone Morphogenetic Protein," *Clin. Ortho. and Related Research*, 429: 139-145 (2004).
Lotz, *Clin. Orthopaedics and Related Res.*, 391S: S108-S115 (2001).
Mellonig, James. "Bone Allografts in Periodontal Therapy," *Clin. Ortho. and Related Research*, 324: 116-125 (1996).
Mellonig, "Decalcified freeze-dried bone allograft as an implant material in human periodontal defects," *The Int'l Journal of Periodontics and Restorative Dentistry*, pp. 41-45 (1984).
Miloslav et al., "Autolyzed antigen-extracted allogeneic bone for bridging segmented diaphyseal bone defects in rabbits," *Clinical Orthopaedics and Related Research*, 229: 249-256 (Apr. 1988).
Nade et al. "Decalcified Bone as a Substrate for Osteogenesis," *Bone Joint Surg.* 59(2): 189-1996 (1977).
Neigel et al. "Use of Demineralized Bone Implants in Orbital and Craniofacial Reconstruction and Review of the Literature," *Opthal. Plast. Reconst. Surg.*, 12:108 (1996).
Nogami et al., "Sustrata Prepared from Bone Matrix for Chondrogenesis in Tissue Culture", *The Journal of Cell Biology*, 62: 510-519 (1974).
Nogami et al., "Transmembrane Bone Matrix Gelatin—Induced Differentiation of Bone", *Calcif. Tiss. Res.*, 19: 153-163 (1975).

(56) References Cited

OTHER PUBLICATIONS

Oberg et al. "Bone formation after implantation of autolysed antigen extracted allogeneic bone in ovariectomized rabbits," *Int. J. Oral Maxillofac. Surg.* 32: 628-632 (2003).
Oberg et al. "Bone healing after implantation of hydroxyapatite granules and blocks (Interpore 200) combined with autolyzed antigen-extracted allogeneic bone and fibrin glue," *Int. J. Oral. Maxillofac. Surg.* 23: 110-114 (1994).
"Organic Reactions", vols. 1-40, John Wiley and Sons, New York, NY (1991).
Ousterhout. "Clinical Experience in Cranial and Facial Reconstruction with Demineralized Bone," *Ann. Plast. Surg.* 15(5): 367-373 (1995).
Paralkar et al., "An EP2 receptor-selective prostaglandin $E_2$ agonist induces bone healing," *PNAS*, 100(11): 6736-6740 (2003).
Peel SA et al., "In search of the ideal bone morphogenetic protein delivery system: in vitro studies on demineralized bone matrix, purified, and recombinant bone morphogenetic protein", *J. Craniofac. Surg.*, 14(3): 284-91 (May 2003).
Ray et al., "Bone Implants," *J. Bone Joint Surgery*, 39A(5): 1119-1128 (1957).
Reddi et al., "Biochemical Sequences in the Transformation of Normal Fibroblasts in Adolescent Rats," *Proc. Natl. Acad. Sci. USA*, 69(6): 1601-1605 (1972).
Ripamonti et al. "Bone induction in a composite allogeneic bone/alloplastic implant," *J. Oral Maxillofac. Surg.* 47: 963-969 (1989).
Ripamonti et al. "The induction of bone in osteogenic composites of bone matrix and porous hydroxyapatite replicas: Experimental study on the baboon," *Oral Maxillofac. Surg.* 9: 817-830 (1991).
Ripamonti. "Bone induction in nonhuman primates: an experimental study on the baboon," *Clin. Ortho. and Related Research*, 269: 284-294 (Aug. 1991).
Ripamonti. "Calvarial regeneration in primates with autolyzed antigen-extracted allogeneic bone," *Clin. Ortho. and Related Research*, 282: 293-303 (Sep. 1992).
Rodd, "Chemistry of Carbon Compounds", vols. 1-5 and supplementals, Elsevier Science Publishers, Amsterdan (1989).
Ronningen et al. "Bone formation enhanced by induction," *Acta Orthop Scan* 56: 67-71 (1985).
Ronningen et al. "Osteogenesis promoted by bone matrix combined with marrow," *Acta Orthop Scand* 5Z: 15-18 (1986).
Rosenquist et al. "Effects of bone grafting on maxillary bone healing in the growing pig," *J. Oral Maxillofac. Surg.* 40: 566-569 (1982).
Rosenthal et al. "Demineralized bone implants for nonunion fractures, bone cysts, and fibrous lesions," *Clin. Ortho. and Related Research* 362: 61-69 (1999).
Russell et al., "Clinical Utility of Demineralized Bone Matrix for Osseous Defects, Arthrodesis, and Reconstruction; Impact of Processing Techniques and Study Methodology," *Orthopaedics*, 22(5): 524-531 (May 1999).
Sailer et al. "Application of purified bone morphogenetic protein (BMP) in cranio-maxillo-facial surgery," *Jour. of Cranio-Maxillo-Facial Surgery* 22: 2-11 (1994).

Sambrook, et al. Molecular Cloning: A Laboratory Manual, 3$^{rd}$ ed., Cold Spring Harbor Laboratory Press, Cold Spring Harbor (2001).
Sampath and Reddi, "Homology of bone-inductive proteins from human, monkey, bovine, and rat extracellular matrix," *Proc. Nat. Acad. Sci.* 80:6591-6594 (1983).
Sampath et al., "Bovine osteogenic protein is composed of dimmers of OP-1 and BMP-2A, Two members of the transforming growth factor-beta superfamily," *J. Biol. Chem.*, 5:265(22): pp. 13198-13205 (Aug. 1990).
Sampath et al., "Isolation of osteogenin, an extracellular matrix-associated, bone-inductive protein, by heparin affinity chromatography," *Proc. Natl. Acad. Sci.* 84(7): 7109-7113 (1987).
Schmid et al. "Osteoinduction in tibial defects in the dog," *Unfallchirurgie* 19: 1-8 (1993).
Schwarz et al., "Dog bone less osteogenetic than rat bone," *Acta. Orthop. Scan.* 60(6): 693-695 (1989).
Schwarz et al. "Decalcified and undecalcified cancellous bone block implants do not heal diaphyseal defects in dogs," *Arch. Orthop. Trauma Surg.* 111:47-50 (1991).
Serini et al., "Class 3 semaphorins control vascular morphogenesis by inhibiting integrin function," *Nature*, 424:391-397 (Jul. 2003).
Smith, Michael et al. "March's Advanced Organic Chemistry", 5$^{th}$ edition, John Wiley and Sons, New York, NY (Mar. 2001).
Steadman et al., "Microfracture: Surgical Technique and Rehabilitation to Treat Chondral Defects", *Clin. Orthop.*, 391 S:362-369 (2001).
Steiner, D.F., "The proprotein convertases," *Curr. Opinion Chem. Biol.* 2: 31-39 (1998).
Temenoff et al., "Effect of poly(ethylene glycol) molecular weight on tensile and swelling properties of oligo(poly(ethylene glycol) fumarate) hydrogels for cartilage tissue engineering", *OPF Hydrogel Material Properties*, John Wiley & Sons, Inc., pp. 429-437 (2001).
Terashima et al., Chondrogenesis in Outgrowths of Muscle Tissue onto Modified Bone Matrix in Tissue Culture, *Clinical Orthopaedics and Related Research*, 127: 248-256 (Sep. 1977).
Todescan et al., "A Small Animal Model for Investigating Endosseous Dental Implants: Effect of Graft Materials on healing of Endoss, Porous-Surfaced Implants Placed in a Fresh Extraction Socket," *The Journal of Oral and Maxillofacial Implants*, 2(2): 217-223 (1987).
Toriumi et al. "Demineralized Bone," Arch Otolaryngol Head Neck Surg. 116: 676-680 (Jun. 1990).
Wise, D.L., "Encyclopedia Handbook of Biomaterials and Bioengineering Part B", Applications New York: Marcel Decker (1995).
Xiaobo et al., "Experimental and Clinical Investigations of Human Insoluble Bone Matrix Gelatin," *Clin. Orthopaedics and Related Research*, 293: 360-365 (1993).
Young et al. "Morphological changes of autoclaved autogenic bone implantation and autoclaved autogenic bone supplemented with allogenic demineralized bone matrix in rat parietal bone," *Histol Histopathol.* 11: 361-369 (1996).
Zhang et al., "A Quantitative assessment of osteoinductivity of human demineralized bone matrix," *J. Periodontal*, 68(11): 1076-84 (Nov. 1997).

\* cited by examiner

DELIVERY SYSTEM

CROSS REFERENCE TO RELATED APPLICATIONS

This application claims benefit of priority to U.S. Provisional Application No. 60/948,866 filed Jul. 10, 2007; U.S. Provisional Application No. 61/040,531 filed Mar. 28, 2008 and U.S. Provisional Application No. 61/040,537 filed Mar. 28, 2008, the contents of all of which are hereby incorporated in their entirety by reference.

FIELD

A delivery system for delivering a substance or material to a surgical site is provided. More particularly, a delivery system comprising a covering and a substance, the covering being configured for at least partially retaining the substance provided therein until the delivery system is placed at a surgical site, and thereafter facilitating transfer of the substance or surrounding materials, is provided.

BACKGROUND

The use of bone grafts and bone substitute materials in orthopedic medicine is known. While bone wounds can regenerate without the formation of scar tissue, fractures and other orthopedic injuries take a long time to heal, during which time the bone is unable to support physiologic loading unaided. Metal pins, screws, rods, plates and meshes are frequently required to replace the mechanical functions of injured bone. However, metal is significantly more stiff than bone. Use of metal implants may result in decreased bone density around the implant site due to stress shielding. Physiologic stresses and corrosion may cause metal implants to fracture. Unlike bone, which can heal small damage cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells.

Conventionally, bone tissue regeneration is achieved by filling a bone repair site with a bone graft. Over time, the bone graft is incorporated by the host and new bone remodels the bone graft. In order to place the bone graft, it is common to use a monolithic bone graft or to form an osteoimplant comprising particulated bone in a carrier. The carrier is thus chosen to be biocompatible, to be resorbable, and to have release characteristics such that the bone graft is accessible. Generally, the formed implant, whether monolithic or particulated and in a carrier, is substantially solid at the time of implantation and thus does not conform to the implant site. Further, the implant is substantially complete at the time of implantation and thus provides little ability for customization, for example by the addition of autograft.

The use of bone grafts is generally limited by the available shape and size of grafts. Bone grafts using cortical bone remodel slowly because of their limited porosity. Traditional bone substitute materials and bone chips are more quickly remodeled but cannot immediately provide mechanical support. In addition, while bone substitute materials and bone chips can be used to fill oddly shaped bone defects, such materials are not as well suited for wrapping or resurfacing bone.

Thus, it would be useful to provide a delivery system for delivering a substance, such as bone graft, to a surgical site that conforms to the surgical site, that maintains a substance provided therein in a coherent mass, and that can be customized at the time of implantation.

SUMMARY

A delivery system for delivering a substance or material to a surgical site is provided. The delivery system comprises a covering and a substance to be retained within and delivered by the covering. Generally, the covering may be a single or multi-compartment structure capable of at least partially retaining a substance provided therein until the covering is placed at a surgical site. Upon placement, the covering facilitates transfer of the substance and/or materials surrounding the surgical site. The covering may participate in, control, or otherwise adjust, the release of the substance or penetration of the covering by surrounding materials, such as cells or tissues.

In accordance with one embodiment, a delivery system is provided comprising a covering having first and second compartments. A first substance may be provided in the first compartment and a second substance (which may be the first substance, another substance, or combinations of these) may be provided in the second compartment. The covering retains the first and second substances for placement at a surgical site and facilitates transfer of the first and second substances or surrounding materials, actively or passively, upon implantation In accordance with a further embodiment, a delivery system is provided comprising a tension band, a covering, and a substance. The substance is provided within the covering and the covering retains the substance for placement at a surgical site. The covering facilitates transfer of the substance or surrounding materials, actively or passively, upon implantation. In some embodiments, the covering forms the tension band.

In accordance with yet a further embodiment, a delivery system is provided comprising a tubular covering. A substance is provided within the tubular covering and the covering retains the substance for placement at a surgical site and facilitates transfer of the substance or surrounding materials, actively or passively, upon implantation. The tubular covering may be subdivided into a plurality of compartments.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

BRIEF DESCRIPTION

FIG. 1b illustrates an alternative view of the delivery system of FIG. 1a.

FIG. 2b illustrates an alternative view of the delivery system of FIG. 2a.

FIG. 5b illustrates a top view of the covering of FIG. 5a.

FIG. 5c illustrates an end cross-sectional view of the covering of FIG. 5a.

FIG. 6b illustrates a top view of the covering of FIG. 6a.

FIG. 6c illustrates an end cross-sectional view of the covering of FIG. 6a.

FIG. 7b illustrates a top view of the covering of FIG. 7a.

FIG. 7c illustrates an end cross-sectional view of the covering of FIG. 7a.

DEFINITIONS

Figure 1A:
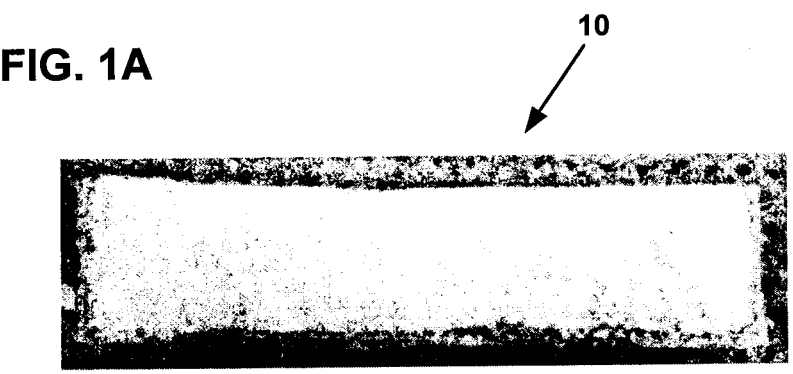
FIG. 1a illustrates a delivery system comprising a relatively narrow tubular covering and a particulated substance, in accordance with one embodiment.

Bioactive Agent or Bioactive Compound, as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., *CRC Press,* 1996; and the United States Pharmacopeia-25/National Formulary-20, published by the United States Pharmcopeial Convention, Inc., Rockville Md., 2001, each of which is incorporated herein by reference.

Biocompatible, as used herein, refers to materials that, upon administration in vivo, do not induce undesirable long-term effects.

Bone, as used herein, refers to bone that is cortical, cancellous or cortico-cancellous of autogenous, allogenic, xenogenic, or transgenic origin.

Demineralized, as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the invention. In some embodiments, demineralized bone has less than 95% of its original mineral content. Demineralized is intended to encompass such expressions as "substantially demineralized," "partially demineralized," and "fully demineralized."

Demineralized bone matrix, as used herein, refers to any material generated by removing mineral material from bone tissue. In preferred embodiments, the DBM compositions as used herein include preparations containing less than 5% calcium and preferably less than 1% calcium by weight. Partially demineralized bone (e.g., preparations with greater than 5% calcium by weight but containing less than 100% of the original starting amount of calcium) are also considered within the scope of the invention.

Osteoconductive, as used herein, refers to the ability of a non-osteoinductive substance to serve as a suitable template or substance along which bone may grow.

Osteogenic, as used herein, refers to the ability of an agent, material, or implant to enhance or accelerate the growth of new bone tissue by one or more mechanisms such as osteogenesis, osteoconduction, and/or osteoinduction.

Osteoimplant, as used herein, refers to any bone-derived implant prepared in accordance with the embodiments of this invention and therefore is intended to include expressions such as bone membrane, bone graft, etc.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," *Clinical Orthopaedics & Rel. Res.,* 357:219-228, December 1998, incorporated herein by reference.

Superficially demineralized, as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

DETAILED DESCRIPTION

I. Introduction

A delivery system for delivering a substance or material to a surgical site is provided. The delivery system comprises a covering and a substance wherein the substance is provided within the covering for delivery to the surgical site. Generally, the covering may be a single or multi-compartment structure capable of at least partially retaining a substance provided therein until the covering is placed at a surgical site. Upon placement, the covering facilitates transfer of the substance and/or materials surrounding the surgical site. The covering may participate in, control, or otherwise adjust, the release of the substance or penetration of the covering by surrounding materials, such as cells or tissues.

In some embodiments, the covering may be used for containment of particulate or morselized materials (the substance provided in the covering), optionally to provide a focus or concentration of biological activity. In some embodiments, the covering may be used for maintaining materials (the substance provided in the covering) in spatial proximity to one another, possibly to provide a synergistic effect. In some embodiments, the delivery system may be used to control availability of a substances provided within the delivery system to cells and tissues of a surgical site over time. In some embodiments, the delivery system may be used for delivery through a limited opening, such as in minimally invasive surgery or mini-open access. In some embodiments, the delivery system may be used to deliver morselized or particulated materials (the substance provided in the covering) in pre-measured amounts. In other embodiments, the substance may be liquid or flowable, or combinations of these with particulate, morselized, and/or other materials.

In various embodiments, the covering may contain a substance or material such as a graft material. The covering limits, and in some embodiments eliminates graft migration and maintains graft density. The delivery system, with contained substance or material, may be configured to conform to surrounding bony contours or implant space. In some embodiments, the delivery system provides a pathway for healing/cell penetration and tissue ingrowth. Thus, the covering may facilitate transfer of a substance out of the covering or transfer or surrounding materials at the surgical site, such as cells and tissues, into the covering.

The covering may have a single compartment or may have a plurality of compartments. Thus, in one embodiment, the covering is dual-compartment and comprises first and second compartments. A first substance may be provided in the first compartment and a second substance may be provided in the second compartment. The second compartment may be adjacent to, apart from, inside, or surrounding the first compartment. Materials forming the first compartment and the second compartment may be the same or different. Selection of materials, positioning of the compartments, and other factors relating to the first and second compartments may be chosen to achieve simultaneous or sequential delivery or release of a substance or substances.

II. Covering Material

The covering may comprise a structural material and, in some embodiments, a functional material. The structural material may comprise a mesh material, a polymeric material, or other. The functional material may comprise, for example, a radiopaque material, a bacteriocidal material, or other.

Structural Material Characteristics

In various embodiments, in accordance with the specific application for which the covering is being used, the covering may be rigid, may be flexible, may be non-elastic, or may be elastic. The covering material may be braided, woven, non-woven shape memory, particulate, threaded, porous, or non-porous.

The covering may participate in, control, or otherwise adjust the release of the substance. For example, the covering may act as a selectively permeable membrane and/or may be porous, with the level of porosity being related to the nature of the substances inside the covering. Thus, the material for and configuration of the covering may be selected or adjusted based on desired release characteristics. Specific properties that may be adjusted include thickness, permeability, porosity, strength, flexibility, elasticity, and others of the covering material. It is to be appreciated that some of these properties may depend on others. For example, the thickness and porosity of the material may contribute to its strength, flexibility, and elasticity.

In some embodiments, the covering may be porous to fluid and/or cells, may be biocompatible, and may be resistant to rupture (including should the substance provided therein swell). In some embodiments, the covering with the substance provided therein may be loadbearing. The covering may be resorbable or non-resorbable. The covering may provide increased handling properties, may have irrigation resistance, and/or may support cellular penetration. Flexibility of the covering may be selected to suit particular applications. In some applications, it may be desirable to have a flexible covering.

If the covering is made from a resorbable material, the covering degrades and disappears after a period of time. If the covering is not made of a resorbable material, the covering remains in the body. Tissue ingrowth may occur to bind the host tissue to the substance provided within the covering. Tissue ingrowth through and around the covering, between the host tissue and the substance provided within the covering, may be promoted via openings in the covering.

In various embodiments, the covering may comprise a porous material or a mesh material. The size of the pores of the covering may be designed to permit cellular infiltration (approximately several microns to several millimeters), but may also be designed specifically to exclude cells for the inside of the covering (e.g. approximately 0.45 microns) and only allow diffusion of small molecules (proteins and hormones). Thus, the covering may act to control access to the interior of the delivery system by cells. In embodiments comprising more than one compartment, characteristics of the covering material may be varied between compartments. Generally, the porosity, flexibility, strength, or any other characteristic of one compartment may vary from that characteristic of the other compartment. U.S. Patent Application Publication No. 2005/0283255 for Tissue-Derived Mesh for Orthopedic Regeneration describes suitable manners for forming a mesh for use with a covering as provided herein and is herein incorporated by reference in its entirety.

The covering may be formed of a resorbable or nonresorbable, natural or synthetic biocompatible material. In some embodiments, more than one material may be used, including as multiple layers. For example, in an embodiment comprising two compartments, one or more materials may be used for the first compartment and a different material or materials may be used for the second compartment. For example, one compartment or portions thereof may be made of material or materials that provide a desired property or properties relative to other compartments or portions thereof, such as increased or decreased resorbability or stiffness, or the different compartments or portions thereof may be imparted with different drug delivery properties, etc. Alternatively, all compartments may comprise the same material or mixtures of materials. Where the characteristics of the material are varied between compartments, or over the surface of a single compartment, the pores of the first compartment or portion thereof may be larger than the pores of the second compartment.

The covering may comprise any suitable structure for delivering a substance in vivo. Thus, as described, the covering may comprise a mesh. In other embodiments, the covering may comprise a polymeric structure with a chamber provided therein. The chamber may be filled with a substance for delivering in vivo, such as autograft, demineralized bone matrix, or others disclosed herein.

In some embodiments, the covering may expand when placed in the body. Expansion can be provided in at least two ways: the covering may be compressed such that the covering expands when placed in the body or the covering may be made of a material that expands when it comes in contact with water or other bodily fluids, either by way of liquid absorption, or by stretching when the materials inside it absorb liquid and themselves expand. In some embodiments, the covering may comprise a shape memory material such as copper-zinc-aluminum-nickel alloy, copper-aluminum-nickel alloy, and nickel-titanium (NiTi) alloy. Reinforcing materials such as cortical bone, calcium phosphates, etc. may be incorporated into the structure of the covering to reinforce it.

The covering may be configured for specific compressive strength and rigidity by adjusting density and resorption time of the covering. In some embodiments, a coating may be provided over the covering. For example, the coating may be a compound of poly-L-lactide, of polyglycolic acid, or their polymers. The coating may be selected such that it has a resorption time wherein it is resorbed by the body and the material within the covering is permitted to exit through openings in the covering.

Exemplary Covering Materials

Polymeric material (for example, see U.S. Pat. Nos. 6,696,073, 6,478,825, 6,440,444, and 6,294,187 and U.S. Patent Publications Nos. 2006/0216323 and 2005/0251267, all herein incorporated by reference in their entirety); woven materialand braided material (for example, see U.S. Patent Publication No. 2005/0283255, herein incorporated by reference in its entirety); non-woven; shape memory material; using outer particles to contain inner particles; attach particles to threads; add porosity to mesh fibers; non-porous materials; non-porous materials.

In some embodiments, the covering may comprise a mesh material. Suitable mesh materials include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly (glycolic acid) (PGA), poly(lactic acid-glycolic acid) (PLGA), polydioxanone, PVA, polyurethanes, polycarbonates, and others. Other suitable materials include carbon fiber, metal fiber, and various meshes. In other embodiments, the covering may comprise non-woven material such as spun cocoon or shape memory materials having a coil shape or shape memory alloys.

Generally, the covering may be formed of any natural or synthetic structure (tissue, protein, carbohydrate) that can be used to form a covering configuration. Thus, the covering may be formed of a polymer (such as polyalkylenes (e.g., polyethylenes, polypropylenes, etc.), polyamides, polyesters, poly(glaxanone), poly(orthoesters), poly(pyrolicacid), poly (phosphazenes), polycarbonate, other bioabsorbable polymer such as Dacron or other known surgical plastics, a natural biologically derived material such as collagen, gelatin, chitosan, alginate, a ceramic (with bone-growth enhancers, hydroxyapatite, etc.), PEEK (polyether-etherketone), dessicated biodegradable material, metal, composite materials, a biocompatible textile (e.g., cotton, silk, linen), extracellular matrix components, tissues, or composites of synthetic and natural materials, or other. Various collagen materials can be used, alone or in combination with other materials, including collagen sutures and threads. Any suitable collagen material may be used, including known collagen materials, or collagen materials as disclosed in U.S. patent application Ser. No. 12/030,181, filed Feb. 12, 2008, hereby incorporated by reference in its entirety, which discloses collagen materials that may be used for forming a covering. Some examples include polymer or collagen threads woven, or knitted into a mesh. Other suitable materials include thin polymer sheets molded in the presence of a porogen and having underwent leaching; polymer sheets or naturally derived sheets such as fascia and other collagen materials, small intestinal submucosa, or urinary bladder epithelium, the sheets being punctured to introduce porosity; specific shapes printed using available or future printing technologies; naturally secreted materials such as bacterial cellulose grown within specific molds; etc.

In some embodiments, mesh fibers may be treated to impart porosity to the fibers. This may be done, for example, to PLA, PLGA, PGA, and other fibers. One suitable method for treating the mesh fibers comprises supercritical carbon dioxide treatment to partially solubilize the particles. This treatment may further be carried out for viral inactivation. Another suitable method for treating the mesh fibers comprises explosive decompression. Explosive decompression generates porosity and leads to controlled permeability. The mesh material further may be loaded with cells, growth factors, or bioactive agents.

In further embodiments, fibers of a mesh material may be treated such as by having particles adhered thereto. The particles may be, for example, bone particles. Thus, in one embodiment, the covering may comprise a plurality of threads formed into a fabric. The threads may have particles adhered thereto. For example, the threads may have particles strung on the thread. In an alternative embodiment, the covering may be formed of a material and the material may be coated with particles.

In yet other embodiments, the covering may comprise a non-porous material, which may be permeable. A non-porous material may be used for later (or delayed) delivery of a substance provided therein. Such substance may comprise, for example, cells, growth factors, or bone morphogenetic proteins. Accordingly, in one embodiment, a delivery system for delayed delivery of cells, growth factors, or bone morphogenetic proteins is provided comprising a non-porous covering.

Functional Material Characteristics

The covering material may have functional characteristics. Alternatively, other materials having functional characteristics may be incorporated into the covering. Functional characteristics may include radiopacity, baceriocidity, source for released materials, etc.

Suitable radiopaque materials include, for example, ceramics, mineralized bone, ceramics/calcium phosphates/calcium sulfates, metal particles, fibers, and iodinated polymer (see, for example, WO/2007/143698). Suitable bacteriocidal materials may include, for example, trace metallic elements. In some embodiments, trace metallic elements may also encourage bone growth.

The covering itself may be designed to release materials during degradation of the covering material. Thus, bone morphogenic proteins (BMPs), growth factors, antibiotics, angiogenesis promoting materials (discussed more fully below), bioactive agents (discussed more fully below), or other actively releasing materials may be incorporated into the covering material such that as the covering material is degraded in the body, the actively releasing material is released. For example, an actively releasing material may be incorporated into a biodegradable polymer covering such as one manufactured of a biodegradable polyester such as poly (lactic acid) (PLA), poly(glycolic acid) (PGA), or poly(lactic-co-glycolic acid) (PLGA). In some embodiments, poly (ethylene glycol) (PEG) may be incorporated into the biodegradable polyester to add hydrophilic and other physico-chemical properties to enhance drug delivery. In some embodiments, composites of allograft bone and biodegradable polymers (for example, PLEXUR® products available from Osteotech) may be used in the covering.

In one embodiment of a covering comprising two compartments, first and second materials may be used for the first and second compartments, respectively. The first material may release a growth factor according to a first rate and the second material may release a growth factor according to a second rate. Further, the growth factors released by the first and second compartments may be the same or may be different. For example, an angiogenic growth factor may be provided with the first compartment and an osteoinductive growth factor may be provided with the second compartment.

Mesh Formulation

Any suitable technique may be used for forming a material for the covering. In one embodiment, elongated bone-derived particles or fragments of small intestinal submucosa (for example, approximately 6) may be combined longitudinally into three small bundles, each having, for example, from about 1 to about 3 tissue particles. The three bundles may then braided. Various methods of braiding and types of braids any of which may be useful in producing the material of the invention herein are also described, e.g., by Shaw, KNOTS—Useful & Ornamental, Bonanza Books, New York (1983), incorporated herein by reference. The ends of the braided tissue-derived particles may then be glued together using a fixation agent to prevent their unraveling, or they may be held together with a biocompatible polymer or metal band.

In an alternative embodiment, bone-derived particles are combined with a solvent to form a material. Exemplary solvents include water, lower alkanols, ketones, and ethers and mixtures of any of these or other materials. The material may then extruded at an appropriate temperature and pressure to create a thread. Threads may also be produced by spinning, drawing, rolling, solvent-extruding, cutting or laser cutting from a sheet or bar stock. The material may alternatively be cast or molded into a solid sheet or bar stock and then cut into thin threads. These may be used immediately or woven into a mesh. Alternatively or in addition, they may be spliced, wrapped, plied, cabled, braided, woven, or some combination of these. The material may be shaped by thermal or chemical bonding, or both. In one embodiment, a portion of the solvent is removed from the material before extrusion.

Alternatively or in addition, the material may be cast as a slurry, extruded, or molded. A variety of materials processing methods will be well known to those skilled in the art. For example, the material may be solvent cast using a press such as a Carver press to spread the material into a film. Solvent evaporation will yield a porous film. Alternatively, the material may be compression molded into a film. The mesh size or porosity of the film will depend on the thickness of the film and the viscosity of the precursor and can be easily manipulated by one skilled in the art. Where elongated particles are used in an extruded aggregate, they will tend to be aligned roughly parallel to one another.

In an alternative embodiment, a thread of a biocompatible natural or synthetic material, for example, polylactide or collagen, may be coated with tissue-derived or other elements, for example, by dubbing. For example, a polymer fiber may be coated with an adhesive, for example, lecithin, and bone particles or other osteoconductive or osteoinductive fibrils allowed to adhere to the thread. The thread may then be twisted on itself or with a second or a plurality of similarly treated threads. Alternatively or in addition, the threads may be braided. The adhesive may be a lipid that is waxy at room temperature, for example, a di- or triglyceride that is solid at room temperature. Alternatively or in addition, the adhesive may be a phosphocholine or phosphatidylcholine. In some embodiments, the adhesive is a material that binds both the thread and the material that is used to coat the thread (e.g., bone particles) but that does not degrade either. Non-aqueous adhesives may improve the stability of the final aggregate as compared to aqueous adhesives.

Suitable may be formed utilizing well known techniques, e.g., braiding, plying, knitting, weaving, felting, that are applied to processing natural fibers, e.g., cotton, silk, etc., and synthetic fibers made from synthetic bioabsorbable polymers, e.g., poly(glycolide) and poly(lactic acid), nylon, cellulose acetate, etc. See, e.g., Mohamed, American Scienitist, 78: 530-541 (1990). For example, U.S. Pat. No. 5,378,469, herein incorporated by reference in its entirety, describes the braiding of crosslinked and noncrosslinked collagen threads using a harness braiding machine (New England Butt Co., Providence, R.I.). Specifically, collagen thread is wound onto cylindrical stainless steel spools. The spools are then mounted onto the braiding carousel, and the collagen thread is then assembled in accordance with the instructions provided with the braiding machine. In one particular run, a braid was formed of four collagen threads, which consisted of two threads of uncrosslinked collagen and two threads of crosslinked collagen. One skilled in the art will recognize that these techniques may be applied to the other fibrous materials described herein.

Fibers and more evenly dimensioned particles may also be plied into yarns using the same methods and same machinery known to those skilled in the art in plying threads made out of other material, e.g., cotton, polyester, etc. For example, U.S. Pat. No. 5,378,469 describes the production of a 60 ply yarn from noncrosslinked collagen threads. Four collagen threads were twisted together. Three of the resultant 4-ply strands were then twisted together in the opposite direction, and then 5 of the resultant 12 ply strands were twisted in the opposite direction.

Elongated materials including multistranded materials, e.g., braids, plied yarns, cables, etc., may be knitted into tubular or flat fabrics by using techniques known to those skilled in the art of producing fabrics manufactured from other types of threads. Various biologically active substances can be incorporated in, or associated with, the braided, knitted, or woven materials. Particles and fibers and materials of these (including multistranded materials) may alternatively or additionally be assembled into a material by non-woven methods such as laying, needle-punching, and hooking (as for a rug). For example, a thread may be attached to another thread or a pressed film.

Regardless of the assembly method, the material shape, mesh size, cable thickness, and other structural characteristics, e.g., architecture, may be customized for the desired application. For example, where a two dimensional aggregate is used to retain a thixotropic material within a gap, a tight weave is preferred to prevent leakage. To optimize cell or fluid migration through the mesh, the pore size may be optimized for the viscosity and surface tension of the fluid or the size of the cells. For example, pore sizes on the order of approximately 100-200 µm may be us if cells are to migrate through the mesh. Mesh size may be controlled by physically weaving strands of the material by controlling the ratio of solvent to solids in a precursor material.

Cells may be seeded onto the material. In one embodiment, cells may be encapsulated in a matrix such as alginate or collagen gel and the capsules placed on the material. Methods for encapsulating cells are well known to those skilled in the art; an exemplary method is disclosed in U.S. Pat. No. 4,391,909, herein incorporated by reference in its entirety. Seeded materials generally do not need to be incubated for long periods of time in solutions that could partially dissolve the binding agent. Instead, the capsules may be placed on the material or covering shortly before implantation. In another embodiment, cells are simply mixed with a gel which is then combined with the material. Alternatively, a material or covering may be cultured with cells before implantation. In one embodiment, thicker materials are used for culturing to increase mechanical integrity during implantation. Any class of cells, including connective tissue cells, organ cells, muscle cells, nerve cells, and stem cells, may be seeded onto the implant. In an exemplary embodiment, connective tissue cells such as osteoblasts, osteoclasts, fibroblasts, tenocytes, chondrocytes, and ligament cells and partially differentiated stem cells such as mesenchymal stem cells and bone marrow stromal cells are employed.

III. Covering Configuration or Form

The shape, configuration, or form of the covering may be selected for particular applications. Such shape and configuration may include, for example, the basic shape of the covering (e.g., a cylinder), whether the covering has a single or a plurality of compartments, and whether the covering includes attachment mechanisms. The covering (or delivery system) may be configured to conform to surrounding bony contours of the space in which it is placed.

Form

As previously discussed, the covering may be formed of as a mesh. Thus, the covering may comprise a woven material. The woven material may have varying degrees of permeability. It may be permeable, semi-permeable, or non-permeable. Permeability may be with respect to cells, to liquids, to proteins, to growth factors, to bone morphogenetic proteins, or other. In further embodiments, the material may be braided.

In alternative embodiments, the covering may comprise a substantially solid structure, such as a polymer structure with a chamber, or a spun cocoon.

Shape

The covering may have any suitable configuration. For example, the covering may be formed as a ring, a cylinder, a cage, a rectangular shape, a mesh, a suture-like wrap, a continuous tube, or other configuration. In specific embodiments, the covering may be formed as a thin tube (having, for example, a diameter of approximately 4-6 mm) designed to be inserted through catheters, a rectangular shape designed to fit adjacent to spinal processes for PLF, a cube like structure designed to fit between vertebral bodies or within cages for interbody spinal fusion, a tube like shape where the ends are designed to be fitted onto nonunion long bone defects, relatively flat shapes designed to fill cranial or maxillofacial defects, rectangular structures designed for osteochondral defects, structures preshaped to fit around various implants (e.g. dental, doughnut with hole for dental implants), or relatively elastic ring-like structures that will stretch and then conform to shapes (e.g. rubber band fitted around processes). In an embodiment wherein the covering is formed as a cage, the cage may comprise a plurality of crossed filaments which define between them a series of openings for tissue ingrowth. Any of these shapes may be used for a covering comprising a plurality of compartments. For example, in a tubular embodiment, the tube may be formed into a plurality of compartments by tying a cord around the tube at one or more points, or by other suitable mechanism such as crimping, twisting, knotting, stapling, sewing, or other. The configuration of the covering may be determined by the substance to be provided within the covering. For example, if the substance to be contained comprises fibers, the covering may be formed as strings or sutures that are wrapped around the fibers.

Figure 1B:
Figure 2A:
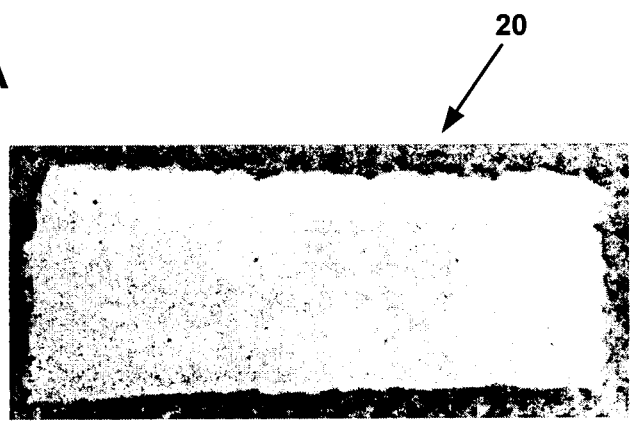
FIG. 2a illustrates a delivery system comprising a relatively wide tubular covering and a particulated substance, in accordance with one embodiment.
Figure 2B:
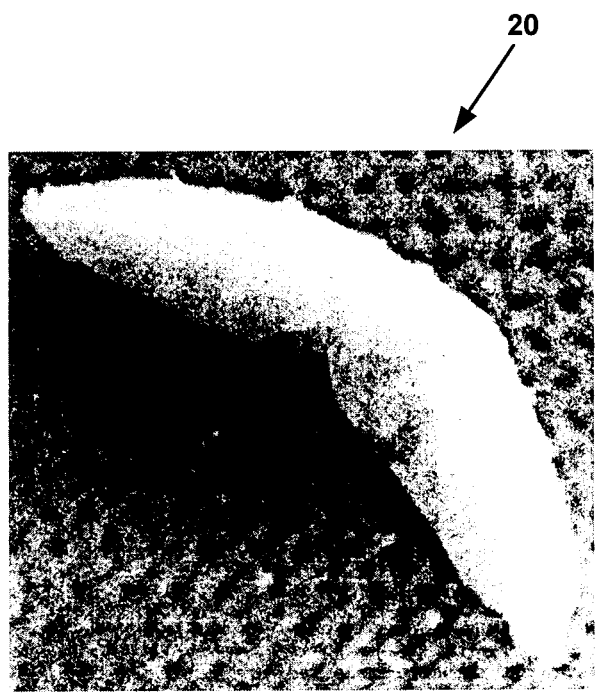

FIGS. 1a and 1b illustrate a delivery system comprising tubular covering 10 and particulated substance. In the embodiment of FIGS. 1a and 1b, the covering 10 is relatively narrow. In contrast, FIGS. 2a and 2b illustrate a delivery system comprising relatively wide covering 20. In the embodiments shown in FIGS. 1a, 1b, 2a, and 2b, the coverings 10, 20 comprise a mesh material. The particulated substance is provided within the coverings 10, 20.

Figure 3:
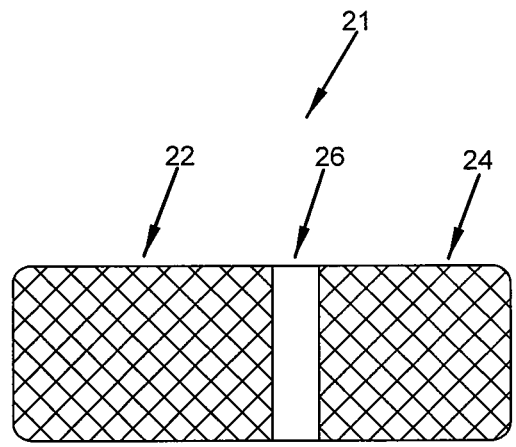
FIG. 3 illustrates a two-compartment covering comprising two single-compartment coverings coupled together, in accordance with one embodiment.

A covering as provided herein may further comprise an attachment or coupling mechanism. Any suitable attachment mechanism can be used, such as a tab, loop, tack or other structure adapted for attachment at the site. Also, for example, a covering may include a hook-and-eye (Velcro) portion. The hook-and-eye portion may be used to couple the covering to a tissue structure, such as bone, or to another covering. For example, as shown in FIG. 3, a dual compartment covering 21 may be formed by two single-compartment coverings 22, 24 coupled at portion 26 at complementary ends thereof. In the embodiment shown, the coupling portion 26 may comprise overlapping/mating Velcro portions. The size and shapes of the single compartment coverings 22, 24 may be the same or may be different. Further, the materials of the compartment coverings 22, 24 and the substances provided therein may be the same or may be different. The coupling may be done pre-implantation or post-implantation. In post-implantation embodiments, the coupling may be done by inserting first and second coverings through an opening into a space and coupling the coverings within the space.

Compartments

Single Compartment

Figure 4:
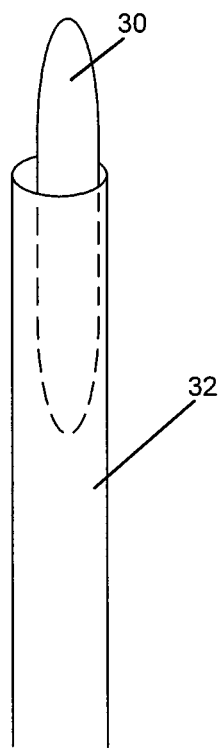
FIG. 4 illustrates a tubular covering for delivery in a catheter, in accordance with one embodiment.

As shown in FIGS. 1a, 1b, 2a, and 2b, the covering may comprise a single compartment covering 10, 20. Those figures illustrated generally tubular embodiments. In further embodiments, such as shown in FIG. 4 the covering 30 may be a narrow tube for delivery through a catheter 32. For example, the covering may be delivered percutaneously using a catheter through which it is inserted. Thus, as shown, the covering 30 may have dimensions suitable for receipt in the catheter. Optionally, the covering 30 may be stiffened to facilitate insertion into the catheter 32. Such stiffening may be achieved through choice of material for the covering, by treating the material of the covering, or other. In some embodiments, the covering 30 may be coated with a material to facilitate sliding engagement with the catheter 32.

Figure 5A:
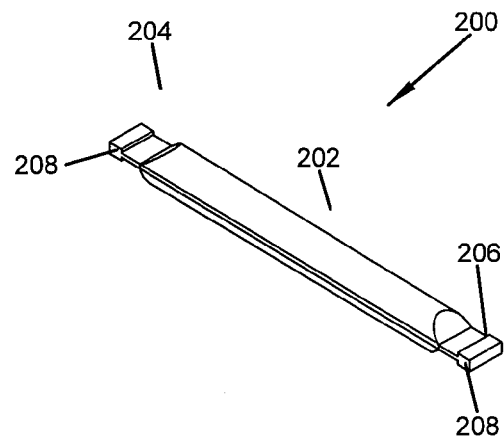
FIG. 5a illustrates a perspective view of a covering having an elongated containment portion, in accordance with one embodiment.
Figure 5B:
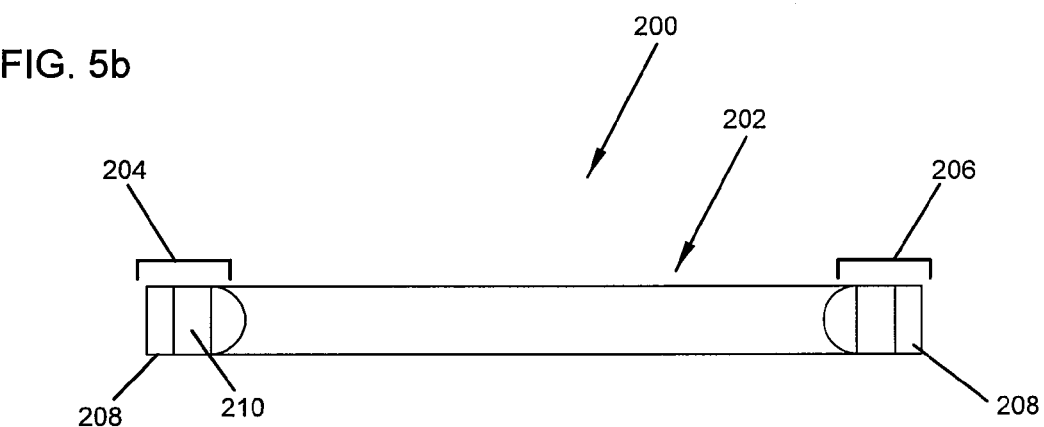
Figure 5C:
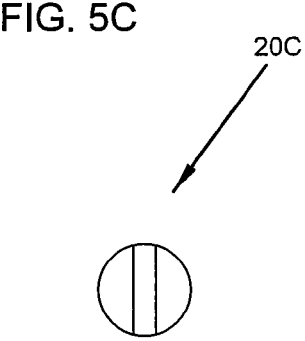

FIGS. 5a-5c illustrate a covering embodiment 200 having an elongated containment portion 202 for housing a substance for delivery, and having first and second ends 204, 206. One or both of the first and second ends 204, 206 may have an attachment mechanism 208. Any suitable attachment mechanism may be used. In the embodiment shown, each of the first and second ends 204, 206 comprises a tab attachment mechanism 208. One or both of the first and second ends 204, 206 further may be sealed. In the embodiment shown, the first end 204 is sealed. The seal 210 may comprise a portion of the tab 108, as shown, or may be separate from the tab 108. The seal 210 may have a width and a thickness suitable for maintaining a seal with the substance provided within the containment portion. For example, the seal 210 may have a length of approximately 0.6 cm, with the tab 208, including the seal 210, having a length of approximately 1.0 cm. Accordingly, the tab 108 is coextensive with the seal 210 for approximately 0.6 cm and extends approximately 0.4 cm beyond an outer edge of the seal 210. In some embodiments, one or both ends 204, 206 may be unsealed such that the covering 200 may be filled with a substance and sealed, for example via heat sealing, in the operating room. The elongated containment portion 202 comprises a length, a width, and a cross section. The length may be, for example, approximately 5 cm, approximately 10 cm, approximately 20 cm, or any other suitable length. The width may be, for example, approximately 1 cm. The length to width ratio may vary depending on application. In the embodiment of FIGS. 5a-5c, the containment portion 202 has a generally circular cross-sectional shape with an approximately 1.0 cm diameter. While exemplary dimensions are provided with respect to FIGS. 5a-5c, these dimensions are intended for illustration only and are not limiting.

Figure 6A:
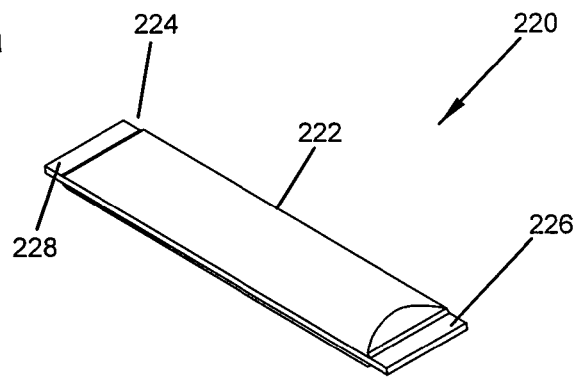
FIG. 6a illustrates a perspective view of an alternative embodiment of a covering having an elongated containment portion.
Figure 6B:
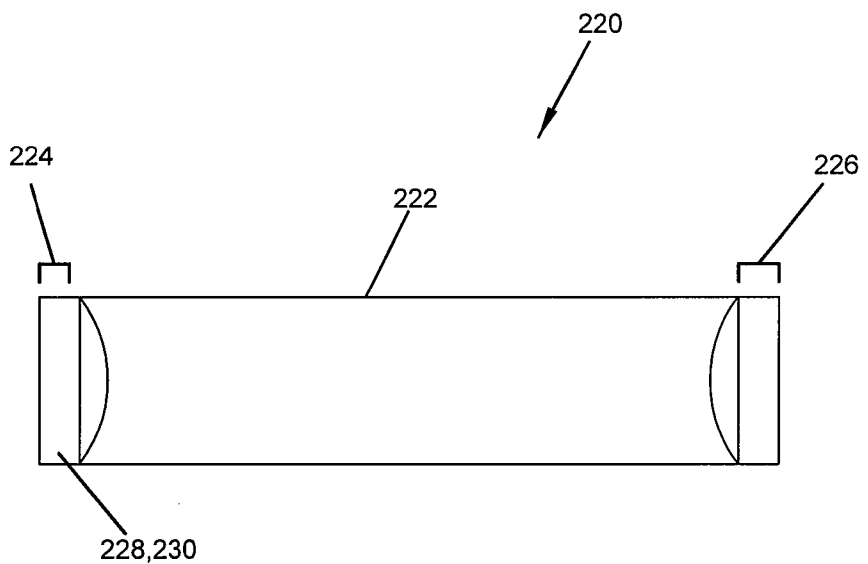
Figure 6C:
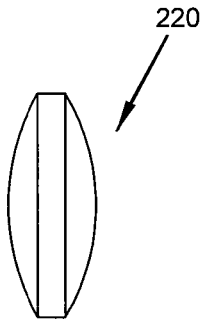

FIGS. 6a-6c illustrate an alternative embodiment of a covering 220 having an elongated containment portion 222 for housing a substance for delivery, and having first and second ends 224, 226. In the embodiment of FIGS. 6a-6c the containment portion 222 has a generally oval cross-sectional shape. In various embodiments, the covering 220 may have a width of approximately 2.5 cm, a containment portion 222 length of approximately 5 cm or approximately 10 cm, and a tab 228 length of approximately 0.5 cm. In the embodiment of FIGS. 6a-6c, a seal 230 is provided at the first end of the covering and extends over substantially the entire length of the tab 228 at the first end 224. While exemplary dimensions are provided with respect to FIGS. 6a-6c, these dimensions are intended for illustration only and are not limiting.

Figure 7A:
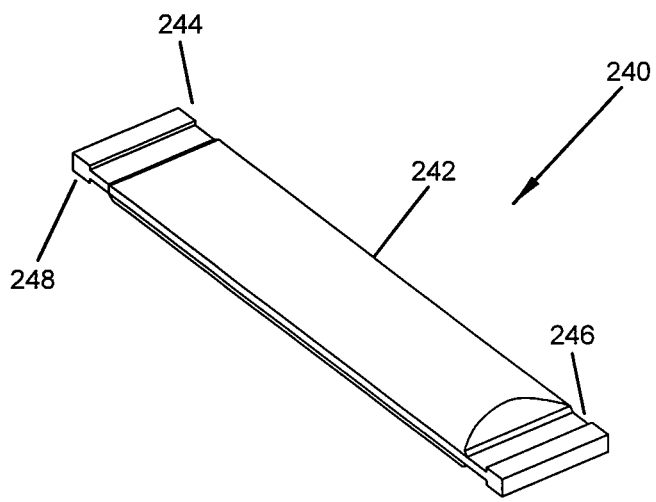
FIG. 7a illustrates a perspective view of yet an alternative embodiment of a covering having an elongated containment portion.
Figure 7B:
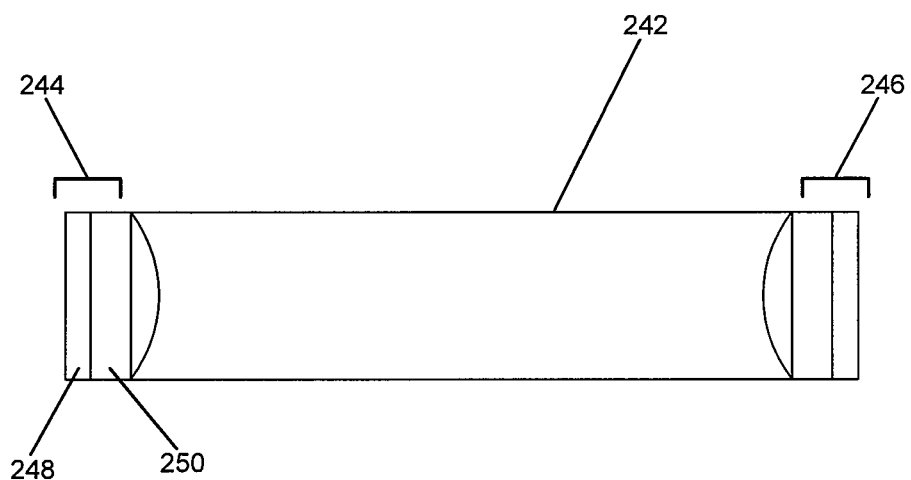
Figure 7C:
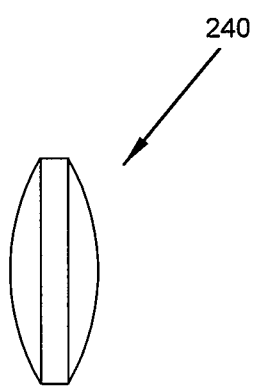

FIGS. 7a-7c illustrate an alternative embodiment of a covering 240 having an elongated containment portion 242 for housing a substance for delivery, and having first and second ends 244, 246. The embodiment of FIGS. 7a-7c is substantially similar to the embodiment of FIGS. 6a-6c except for the tabs 248 at the first and second ends 244, 246. In the embodiment of FIGS. 7a-7c, the tabs 248 have a length of approximately 1.0 cm and the associated seal 250 of the tab at the first end 244 has a length of approximately 0.6 cm. Accordingly, the tab 248 is coextensive with the seal 250 for approximately 0.6 cm and extends approximately 0.4 cm beyond an outer edge of the sea 2501. While exemplary dimensions are provided with respect to FIGS. 7a-7c, these dimensions are intended for illustration only and are not limiting.

FIGS. 5a-5c, 6a-6c, and 7a-7c illustrate various alternative embodiments of a covering having an elongated containment portion for housing a substance for delivery, and having first and second ends. In each of the embodiments shown, the first and second ends include a tab attachment mechanism. In alternative embodiments, only one of the ends may have an attachment mechanism. Further, the attachment mechanism may have an alternative configuration, such as a bore for receiving a screw. FIGS. 5a-5c, 6a-6c, and 7a-7c illustrate generally circular and generally oval cross-sectional shapes. In alternative embodiments, any cross-sectional shape, such as a generally rectangular, generally square, generally star, or any other suitable shape. The length, width, and length-to-width ratio may vary depending on the application for the covering.

In a further single compartment covering embodiment, the covering may be used in a variation of the Masquelet technique. The Masquelet technique is used in long bone trauam applications where there is a large interclarary defect, such as where a segment of a long bone is missing. The Masquelet technique typically comprises two stages, a first stage wherein a spacer is placed and soft tissue forms around the spacer, and a second stage wherein the formed soft tissue is used to cover the bone graft. In some embodiments, a covering such as provided herein may be used for trauma repair in a long bone segmental defect. For example, a relatively large covering may be provided with a substance provided therein suitable for trauma repair where the covering is used to hold the space (excluding soft tissue) in the long bone and have soft tissue form therearound. The second step of the Masquelet technique may be avoided because graft materials are provided when the covering is originally placed.

In one embodiment of a single compartment covering, a plurality of substances may be provided within the covering based on characteristics of the substances. For example, where it is desirable to include a particulated first substance within a material having mesh openings larger than the substance, a second substance may be provided surrounding the particulated first substance to reduce the likelihood of release of particles of the first substance from the mesh. Thus, for example, a particulated first substance and a particulated second substance may be provided wherein the particles of the first substance have a smaller size than the particles of the second substance. A covering is provided comprising a mesh having mesh openings or pores larger than the particles of the first substance. For use, the first substance is provided generally centrally within the covering, the second substance is provided around the first substance and thus between the first substance and the second substance. In further embodiments, the second substanced may be coated, for example via spray coating or solvent casting.

In yet a further embodiment, a single compartment covering may be used as a spacer for nonunion. For example, the covering may be placed in a canal of a long bone.

Multi Compartment

In alternative embodiments, and as briefly discussed with respect to FIG. 3, the covering may comprise a plurality of compartments. For example, the covering may comprise nested coverings, coverings coupled via a temporary barrier, coverings separated with a boundary, and others, described below. In embodiments comprising two compartments, a second compartment may be adjacent, apart from, inside, or surrounding a first compartment. Materials for first compartment and the second compartment (which may be designated first and second substances) may be the same, partially the same, or different. The materials for the first compartment and the second compartment may have different release profiles, different porosities, and other different characteristics. Selection of materials, positioning of the compartments, and other factors relating to the first and second compartments may be chosen to achieve simultaneous or sequential delivery or release of a substance or substances. A first substance may be provided in the first compartment and a second substance may be provided in the second compartment. In some embodiments, an osteoinductive substance may be placed in a compartment generally adjacent tissue being treated as implanted and an osteoconductive substance may be placed in a compartment not adjacent tissue being treated. Release rates for the materials provided in the first compartment and the second compartment may be different. In some embodiments, at least one of the compartments may be unfilled at the time of surgery and autograft or other material may be provided therein in the operating room or at the surgical site. In some embodiments, the covering may form a 3D scaffold.

Figure 8:
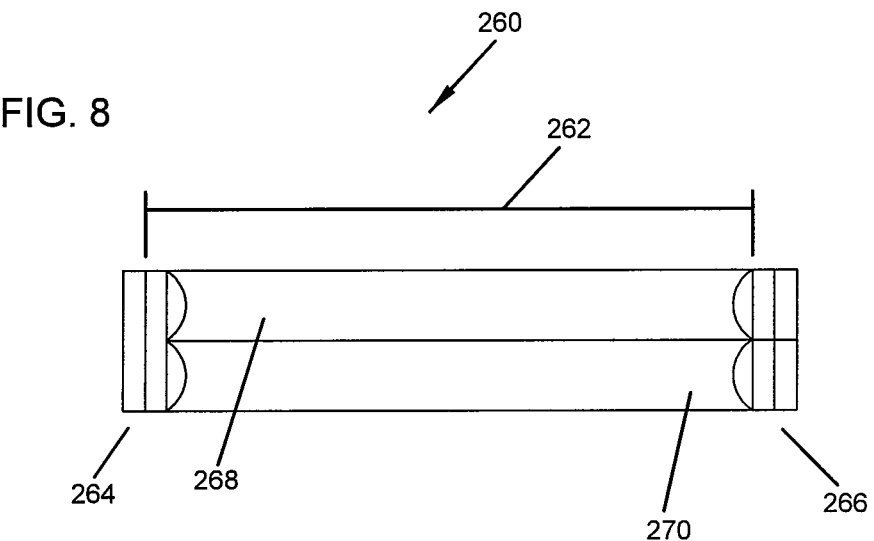
FIG. 8 illustrates a first embodiment of a multi-compartment covering having an elongated containment portion.

The embodiments of FIGS. 5a-5c, 6a-6c, and 7a-7c may further be configured as multi-compartment embodiments. FIG. 8 illustrates an exemplary multi-compartment embodiment of a covering 260 having an elongated containment portion 262 for housing a substance for delivery, and having first and second ends 264, 266. In the embodiment of FIG. 8, the elongated containment portion 262 comprises first and second compartments 268, 270 extending substantially the entire length of the elongated containment portion 262. As shown, the first and second compartments 268, 270 extend side-by-side with each of the first and second compartments 268, 270 extending from the first end 264 of the covering 260 to the second end 266 of the covering 260. Alternatively, the first and second compartments may extend one over the other, such as the first compartment arranged over the second compartment.

Figure 9:
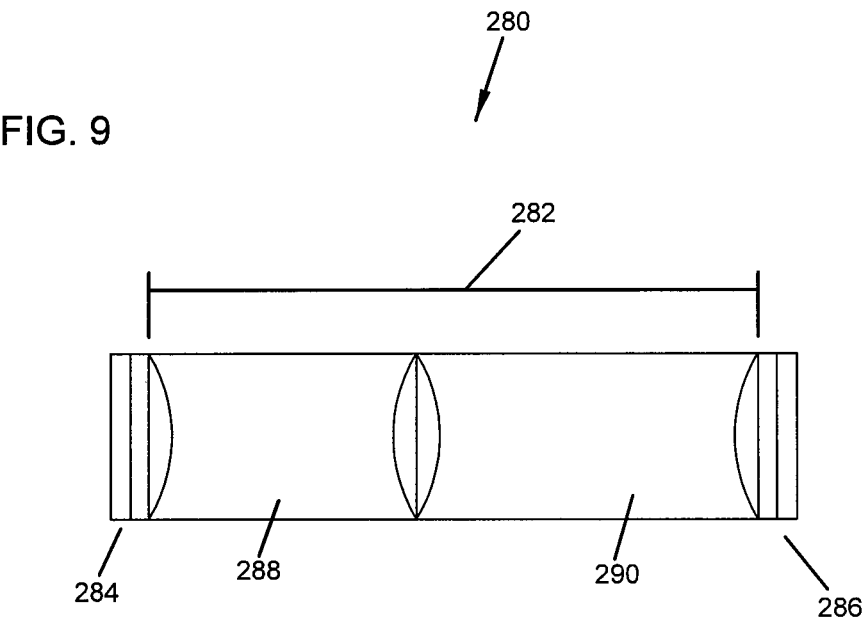
FIG. 9 illustrates a second embodiment of a multi-compartment covering having an elongated containment portion.

FIG. 9 illustrates an exemplary multi-compartment embodiment of a covering 280 having an elongated containment portion 282 for housing a substance for delivery, and having first and second ends 284, 286. In the embodiment of FIG. 9, the elongated containment portion 282 comprises first and second compartments 288, 290 with one compartment 288 provided adjacent the first end 284 and one compartment 290 provided adjacent the second end 286. The compartments 288, 290 may have substantially the same length, as shown, or may have different lengths.

With each of the embodiments of FIGS. 8 and 9, the compartments may be separated by a seal, may communicate therebetween, may be substantially separate, or may be otherwise divided with respect to other multi-compartment embodiments.

Figure 10:
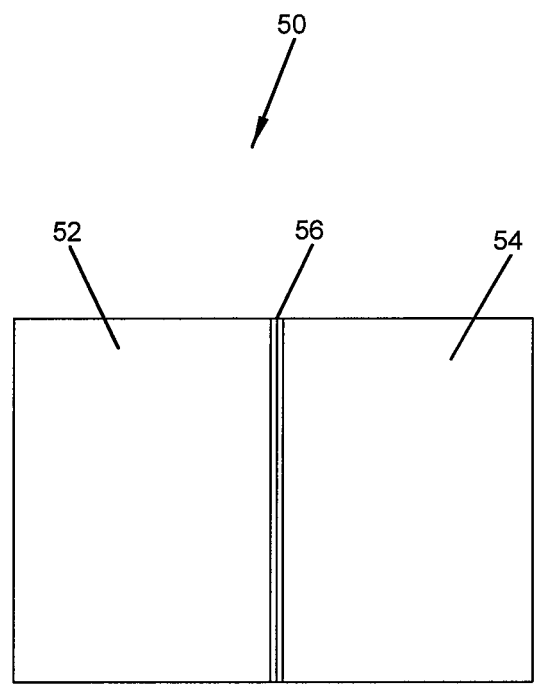
FIG. 10 illustrates a dual-compartment covering comprising first and second compartments situated side-by-side and separated by a barrier, in accordance with one embodiment.

One multi-compartment embodiment, shown in FIG. 10, the covering 50 comprises first and second compartments 52, 54 situated side-by-side and separated by a barrier 56. The barrier 56 may be temporary or may be substantially permanent (remaining for the life of the covering 50). A temporary barrier may be a sheet or a masking agent. A boundary may be provided for dividing between two tissue types, for example between intervertebral disk and bone, between tendon and bone, between meniscus and bone, or between cartilage and bone. The barrier 56 may be integral with the covering 50, integral with one of the first and second compartments 52, 54, or may be coupled to the covering 50 or compartments 52, 54.

Figure 11:
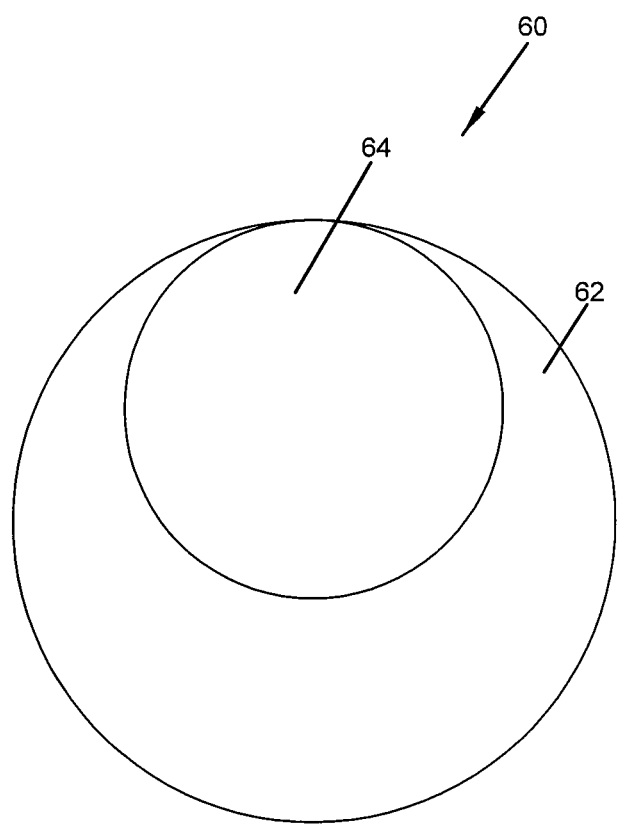
FIG. 11 illustrates a nested dual-compartment covering, in accordance with one embodiment.

FIG. 11 illustrates a nested dual-compartment embodiment 60. As shown, a second compartment 64 is provided within a first compartment 62. Selection of materials for provision in each of the first and second compartments may be based on release kinetics from the first compartment and from the second compartment (provided within the first compartment and thus also within the material provided in the first compartment). In one embodiment, smaller particles of a substance are provided within the first compartment and the first compartment accordingly comprises a tighter mesh while larger particles of a substance are provided within the second compartment and the second compartment comprises a looser mesh. Either or both of the first compartment 62 and the second compartment 64 may be preloaded. Alternatively, either or both of the first compartment 62 and the second compartment 64 may be left empty at manufacture for loading in the operating room or at the surgical site. In one embodiment, the first compartment may be preloaded and a port provided to access the second compartment in the operating room or at the surgical site. In some embodiments, a nesting configuration may comprise a wrapped configuration.

In some embodiments, at least one but not all of the compartments may be weight-bearing. In other embodiments, all of the compartments may be weight-bearing.

Figure 12:
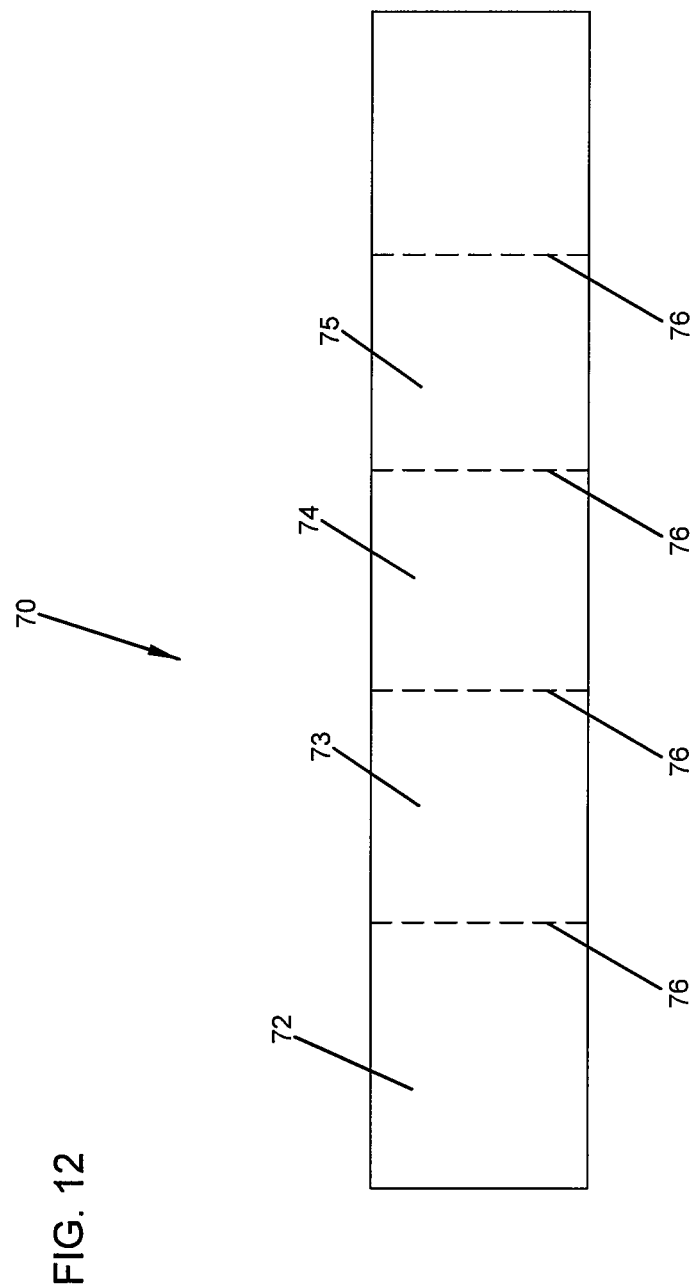
FIG. 12 illustrates a covering comprising as a plurality of compartments separated by perforations, in accordance with one embodiment.

In some embodiments, the covering may be perforated. For example, FIG. 12 illustrates a covering 70 comprising as a plurality of compartments 72, 73, 74, and 75 separated by perforations 76. The surgeon may select the number of compartments desired for placement and cut along a perforation 76 providing that number of compartments. In such embodiment, every other compartment, for example, may be preloaded or filled with a substance for delivery. Alternatively, only some of the compartments may be preloaded, for example, every other compartment may be preloaded such that alternating compartments may be filled in the operating room or at the surgical site.

In another embodiment, the covering may comprise a continuous tube wherein the tube may be twisted to divide portions of the tube. The tube thus may be divided into a series of implants, each having ends that may be twisted or heat treated. Any suitable manner of dividing the tube into a plurality of compartments may be used. For example, the tube may be crimped, heat treated, twisted, knotted, stapled, sewn, or otherwise divided. Any suitable tool may be used for dividing the tube into such compartments including, for example, a crimper, a heat tool, or other.

Any other suitable conformation or shape or combination of these also may be used.

Attachment Mechanisms

The covering may be configured with structures to permit attachment to another covering, to skeletal tissue, or to soft tissue structures. For example, the covering may have tabs, flaps, loops, or other configurations at at least one edge, end, or other portion thereof. In some embodiments, the covering may be provided with attachment mechanisms to facilitate suturing and attachment of the covering in vivo. As previously described, hook-and-eye materials (Velcro) may be used as an attachment mechanism.

In various embodiments, the attachment mechanisms may be integral to the covering. Alternatively, the attachment mechanisms may be secured to the covering, for example, by stitching, welding, crimping, or other. The attachment mechanisms may have any suitable geometric configuration and may optionally include apertures for receiving other components for coupling in vivo, such as an aperture for receiving a screw. Thus, for example, an attachment mechanism may be provided configured for receiving an anchor for fixation to bone. Generally, any number of attachment mechanisms may be provided at any suitable location on the covering.

The attachment mechanisms may be manufactured of the same material as the portion of the covering to which it is coupled or may be manufactured of a different material from the portion of the covering to which it is coupled. The attachment mechanism may be resorbable or nonresorbable. The material of the attachment mechanism may be selected to allow anchoring the covering to an adjacent covering having a complementary attachment mechanism or to another structure. In various embodiments, the attachment mechanism may comprise, allograft, synthetic materials, demineralized bone, nondemineralized bone, other material, or combinations of these. The shape and size of the attachment mechanism may be selected based on application.

In some embodiments, the covering may be tubular and have threaded ends such that the ends may be threaded with a reciprocal thread of a further device or implant. For example, the covering may be used with interference screws. In some embodiments, the covering may include extensions or tabs that may be used for wrapping around or suturing to the surgical site. Alternatively, the covering may be sutured directly to the surgical site. The ends of the covering may be presealed or may sealed after introduction of contents. Sealing may be done by using adhesives, heating, solvent treatment, suturing, knotting, or any other means.

Spinal Tension Band

Figure 13:
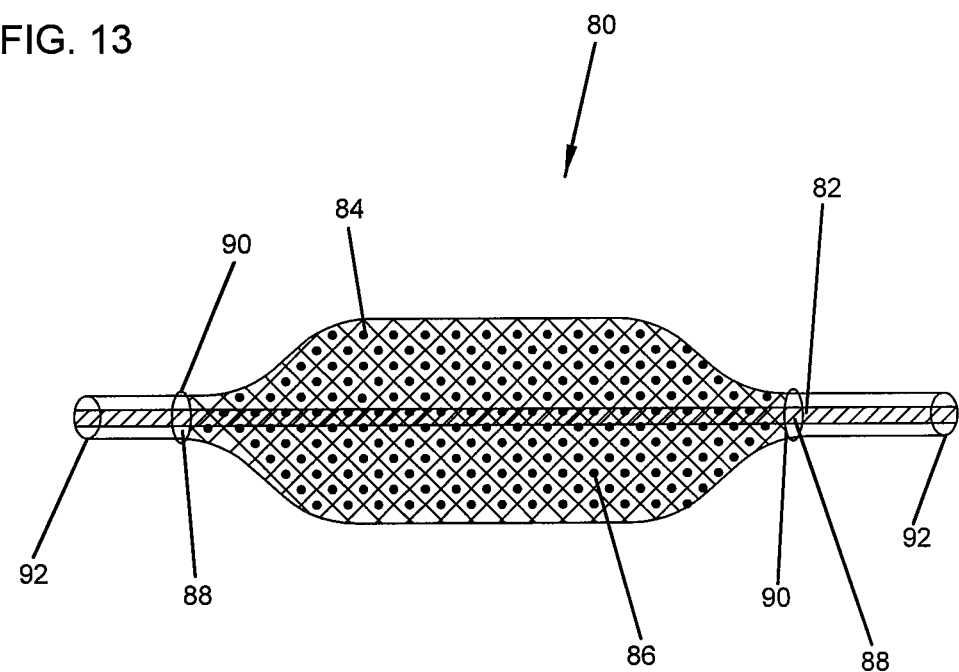
FIG. 13 illustrates a tension band and covering embodiment, in accordance with one embodiment.
Figure 14:
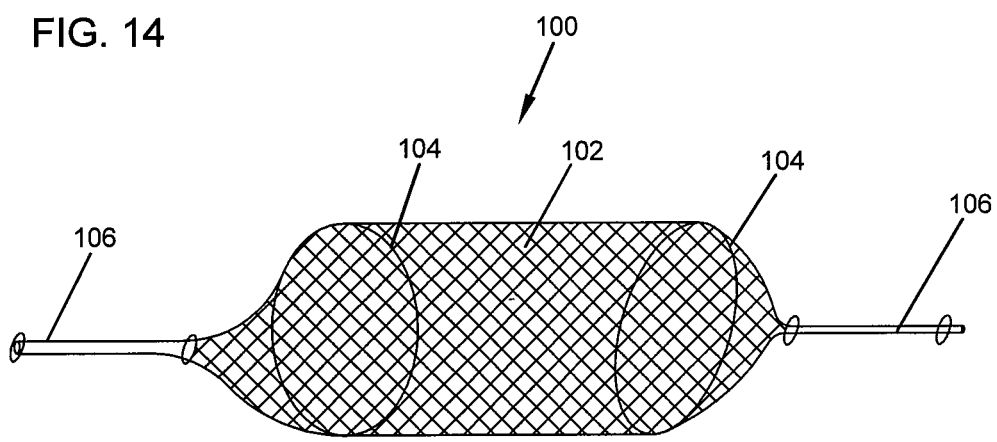
FIG. 14 illustrates tension band comprising covering including spreaders, in accordance with one embodiment.

A further embodiment is shown in FIGS. 13 and 14. Those figures illustrate an embodiment comprising a tension band including a covering for delivering a substance or material. In accordance with the embodiments shown in FIGS. 13 and 14, the covering may comprise any of the materials described herein with respect to other embodiments.

Spinal fusion is frequently used as a treatment for various spinal disorders and is achieved by formation of a bony bridge between adjacent motion segments eliminating the intervertebral joint. Spinal fusion can be accomplished within the disc space, anteriorly between adjacent vertebral bodies and/or posteriorly between consecutive processes, e.g., transverse processes, laminae or other posterior elements of the vertebrae.

One frequently used spinal fusion technique involves removal of the intervertebral disc and insertion of an anterior supporting structure, e.g., bone grafts, bone substitutes, plugs, bone dowels, cages, and the like, into the intervertebral disc space to prevent collapse of the disc space and promote fusion of the adjacent vertebrae. To ensure proper growth and fusion between the affected adjacent vertebrae, the posterior side of the spine may be stabilized by utilizing a rigid metallic implant, e.g., a plate, rod, wire or strip, which spans the adjacent vertebrae to re-create a load distribution similar to that of the intact spine. These metallic implants are commonly referred to throughout the relevant scientific and medical literature as "tension bands." U.S. Pat. No. 6,752,831 teaches a biocompatible osteogenic band to stabilize the spine and is herein incorporated by reference in its entirety. As taught therein, the osteogenic band may be fabricated in whole or in part from various materials, particularly connective type biological material obtained from human and animal tissues, plants, and insects which include, but are not limited to, e.g., bone, tendon, ligament, silk, collagen, elastin, reticulin, cellulose, alginic acid, chitosan, small intestine submucosa or combinations thereof. The biological material can be autogenic, allogenic, transgenic, or xenogenic in origin.

FIG. 13 illustrates a tension band and covering embodiment 80 comprising a tension band or cable 82 and covering 84. As shown, the covering structure 84 is provided over the tension band or cable 82. The tension band 82 may comprise an osteogenic material, as described above, or may comprise other suitable material such as synthetic polymer, titanium, stainless steel, or other. The covering structure 84 may be filled with a substance 86, as described herein. In some embodiments, the substance 86 may comprise an osteogenic particulate material. The overall dimensions of the tension band and covering delivery system 80 can vary widely depending on the distance between affected vertebrae, the site, and the method of affixation. In some embodiments, the dimensions of the tension band and covering delivery system 80 may range from about 1 cm to about 1 meter in length, or from about 3 cm to about 8 cm in length, from about 2 mm to about 30 mm in thickness, or from about 2 mm to about 10 mm in thickness, and from about 2 mm to about 30 mm in width, or from about 2 mm to about 10 mm in width.

The tension cable or band 82 includes first and second end portions 88 for coupling with first and second end portions 90 of the covering structure 84. Coupling may be achieved in any suitable manner such as by adhesive, by mechanical coupling, or other. The tension cable or band 82 further comprises first and second ends 92 affixing or coupling to the vertebrae. The ends 92 may be cut or machined to include threads, grooves, driver head, fasteners, rivets, screws, bolts, pins, etc., to aid in affixing each end portion of the elongated section to the vertebrae. The tension cable or band and covering structure delivery system 80, including material, may have dimensions such that, as formed, the system 80 extends between and cover the spinal processes at each end of the system 80. The tension cable or band 82 may be affixed to the spinal processes by any of the mans disclosed in U.S. Pat. No. 6,752,831.

FIG. 14 illustrates a tension band and covering embodiment 100 wherein the covering 102 includes spreaders 104 such that the covering 102 forms the tension band. In the embodiment shown in FIG. 13, the covering structure 100 has sufficient strength to support the spine. The spreaders 104 substantially prevent the covering 102 from compressing under load. The covering structure 100 includes first and second ends 106, the ends 106 being formed for affixation to the spinal processes. As shown, the ends 106 may be formed into cable structures. First and second spreaders 104 may be provided proximate first and second ends of the covering structure. The spreaders 104 may have any suitable configuration. In some embodiments, the spreaders may comprise discs. In other embodiments, as shown, the spreaders may comprise rings. The spreaders 104 may be formed of any biocompatible material including, for example, a polymer, a metal, or a natural material such as bone. Generally, flexible spreaders may exhibit less strength under loads.

The tension band and covering embodiments shown in FIGS. 13 and 14 may further comprise a substance or material provided in the covering structure. The substance or material may be osteogenic, such as demineralized bone, provided in fiber, liquified, particulate, chunk, or monolithic form. The substance or material may be an osteogenic protein or extract in a suitable carrier. Generally, the substance or material may be osteoinductive and/or osteoconductive. The substance or material may be any material described herein for provision in a covering.

IV. Substance for Delivery by Covering

A substance is provided in the covering, before or during surgery (as described below), for delivery in vivo. Generally, the substance or material may be homogenous or heterogeneous. The substance or material may be selected to exhibit certain gradients. For example, the substance or material may be selected to exhibit a gradient to guide, lure, or attract cells along a pathway. Such gradient may comprise a cell gradient, a cell type gradient (for example transitioning from bone cells to cartilage cells or transitioning from bone cells to tendon cells), a gradient of conductivity, or a gradient of density/porosity. In some embodiments, the substance or material may comprise a sequence of ingredients.

The covering may be used to deliver a substance comprising any suitable biocompatible material. In specific embodiments, the covering may be used to deliver surface demineralized bone chips, optionally of a predetermined particle size, demineralized bone fibers, optionally pressed, and/or allograft. For embodiments wherein the substance is biologic, the substance may be autogenic, allogenic, xenogenic, or transgenic. Other suitable materials that may be positioned in the covering include, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, demineralized bone matrix, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above. In accordance with one embodiment, the substance is a bone matrix compositions such as described in U.S. patent applications Ser. No. 12/140,044 and U.S. Patent Publications Nos. 2007/0098756 and 2007/0110820 all for Bone Matrix Compositions and Methods, herein incorporated by reference in their entireties. In some embodiments, the substance may be pressed before placement in the covering. A substance provided within the covering may be homogenous, or generally a single substance, or may be heterogeneous, or a mixture of substances.

In some embodiments, the substance may be designed to expand in vivo. U.S. Patent Publications No. 2008/0091270 describes an osteoimplant that expands in vivo and is herein incorporated by reference in its entirety. Such an embodiment may be used to fill a space and create contact with congruent surfaces as it expands in vivo, for example for interbody fusion. Thus, in some embodiments, the delivery system may be used in the disc space, between implants, or inside a cage.

The covering retains the substance in place by pressure against the covering. The covering thus may, in some embodiments, maintain particles of substance in close proximity (for example, where the covering retains a substance comprising bone particles). Generally, the ratio of covering material to substance for placement within the covering may be low. For example, in some embodiments, the ratio of covering material to substance, by weight, may be approximately 1:1,000, 1:100, 1:50, 1:25, 1:1, or any suitable ratio that may be higher or lower than these.

In some embodiments the substance delivered by the covering may include or comprise an additive such as an angiogenesis promoting material or a bioactive agent. It will be appreciated that the amount of additive used may vary depending upon the type of additive, the specific activity of the particular additive preparation employed, and the intended use of the composition. The desired amount is readily determinable by one skilled in the art. Angiogenesis may be an important contributing factor for the replacement of new bone and cartilage tissues. In certain embodiments, angiogenesis is promoted so that blood vessels are formed at an implant site to allow efficient transport of oxygen and other nutrients and growth factors to the developing bone or cartilage tissue. Thus, angiogenesis promoting factors may be added to the substance to increase angiogenesis. For example, class 3 semaphorins, e.g., SEMA3, controls vascular morphogenesis by inhibiting integrin function in the vascular system, Serini et al., *Nature*, (July 2003) 424:391-397, incorporated by reference herein, and may be included in the recovered hydroxyapatite.

In accordance with some embodiments, the substance may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; demineralized bone powder as described in U.S. Pat. No. 5,073,373; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; antidepressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immunosuppressants; permeation enhancers, e.g., fatty acid esters such as laureate, myristate and stearate monoesters of polyethylene glycol, enamine derivatives, alpha-keto aldehydes, etc.; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., *CRC Press,* 1996; and the United States Pharmacopeia-25/National Formulary-20, published by the United States Pharmcopeial Convention, Inc., Rockville Md., 2001.

In one embodiment of a covering comprising two compartments, a first growth factor may be provided for delivery by the first compartment and a second growth factor may be provided for delivery by the second compartment. The first and second growth factors may be provided with other substances. The first and second growth factors may be selected (and placed in respective compartment for positioning in vivo) based on desired characteristics of the growth factor. For example, an angiogenic growth factor may be provided in the first compartment and an osteoinductive growth factor may be provided in the second compartment.

Similarly, the substance delivered by the first compartment and the substance delivered by the second compartment may be selected based on desired characteristics of the compartment according to its placement in vivo. Thus, for example, one compartment may have a substance that is substantially osteoclast stimulating while another compartment may have a substance that is substantially osteoblast stimulating.

In one embodiment, demineralized bone fibers may be provided in the first compartment and surface demineralized bone chips may be provided in the second compartment. In this embodiment, the demineralized bone fibers may generally provide osteoinductive characteristics and the surface demineralized chips may generally provide osteoinductive and/or osteoconductive characteristics. In use, the covering may be laid flat on the transverse process and positioned such that the first compartment, holding the demineralized bone fibers, is nearest the vertebral body and the second compartment, holding the surface demineralized bone chips, is farther from the vertebral body, or the compartments may be positioned in any other desired configuration. In another embodiment, a covering may comprise first and second compartments wherein autograft may be placed in one of the compartments prior to placement of the covering in vivo, described more fully below. In other embodiments, three or more compartments may be used, as appropriate for the materials being delivered and the application of the compartmented implant. More than one substance may be provided in a compartment. For example, surface demineralized bone chips and demineralized bone fibers may be mixed and provided within a single compartment. Such mixture of substances within a single compartment may be a substantially uniform mix or may be a plurality of substances placed in the compartment separately such that they are substantially unmixed. When multiple compartments are used, each compartment may contain one or more substances. Exemplary substances that may be provided in one or more compartments of the delivery system include cells from the osteogenic precursors, growth factors, angiogenic factors and other active proteins including bone morphogenic proteins, and cellular scaffolding materials of natural or synthetic origin, antibiotics, and other substances described below.

In some embodiments, other medical devices may be provided within the covering. For example, one or more electrical stimulator electrodes may be provided within the covering.

V. Method of Use

The covering delivers the substance or substances in vivo. Such delivery may be active, passive, by diffusion, or other. Active delivery may include the degradation or decomposition of the covering with the interaction of body fluids, extracellular matrix molecules, enzymes or cells. It may also include the cleavage of physical and/or chemical interactions of substance from covering with the presence of body fluids, extracellular matrix molecules, enzymes or cells. Further, it may comprise formation change of substances (growth factors, proteins, polypeptides) by body fluids, extracellular matrix molecules, enzymes or cells.

The covering is loaded with the substance for placement in vivo. The covering may be pre-loaded, thus loaded at manufacture, or may be loaded in the operating room or at the surgical site. Preloading may be done with any of the substances previously discussed including, for example, DBM, synthetic calcium phosphates, synthetic calcium sulfates, enhanced DBM, collagen, carrier for stem cells, and expanded cells (stem cells or transgenic cells). Loading in the operating room or at the surgical site may be done with any of these materials and further with autograft and/or bone marrow aspirate.

Figure 15:
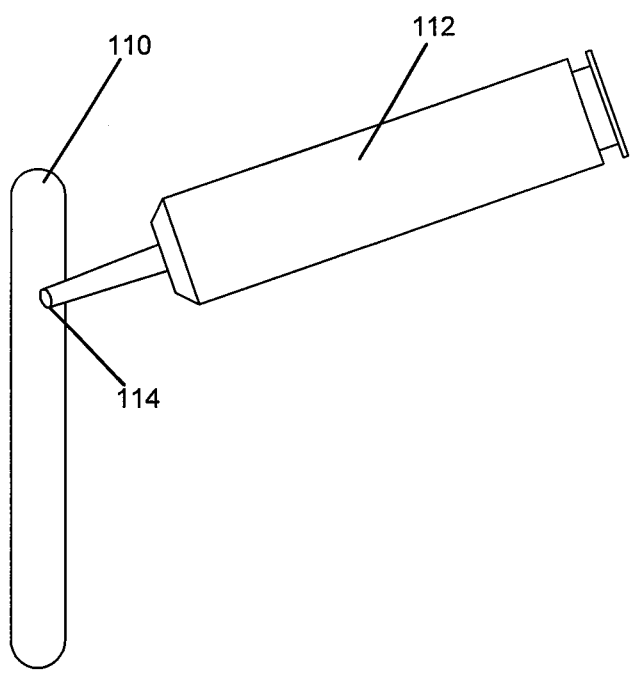
FIG. 15 illustrates a covering being loaded with a substance using a syringe, in accordance with one embodiment.

Any suitable method may be used for loading a substance in the covering in the operating room or at the surgical site. For example, the substance may be spooned into the covering, the substance may be placed in the covering using forceps, the substance may be loaded into the covering using a syringe (with or without a needle), or the substance may be inserted into the covering in any other suitable manner. FIG. 15 illustrates loading the covering 110 with a syringe 112. As shown, in some embodiments, the covering 110 may include a port 114 or other structure for receiving the syringe 112 or similar instrument. Specific embodiments for loading at the surgical site include for vertebroplasty or for interbody space filler.

For placement, the substance or substances may be provided in the covering and the covering placed in vivo. In one embodiment, the covering is placed in vivo by placing the covering in a catheter or tubular inserter and delivering the covering with the catheter or tubular inserter. The covering, with a substance provided therein, may be steerable such that it can be used with flexible introducer instruments for, for example, minimally invasive spinal procedures. For example, the osteoimplant may be introduced down a tubular retractor or scope, during XLIF, TLIF, or other procedures. In other embodiments, the covering (with or without substance loaded) may be placed in a cage, for example for interbody fusion.

Figure 16:
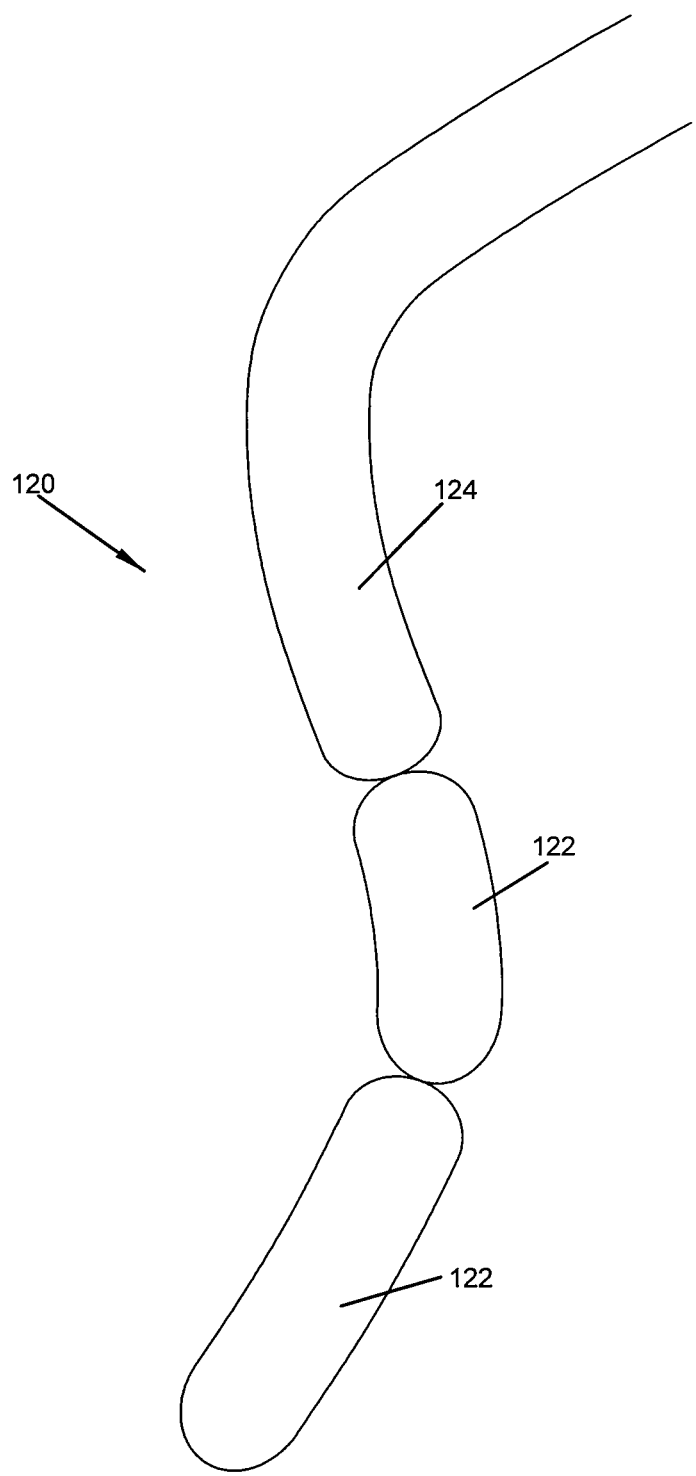
FIG. 16 illustrates a tubular covering partially divided into compartments, in accordance with one embodiment.

In continuous tube embodiments, the surgeon may divide the tube into the desired number of compartments, using a crimper, heat tool or other. FIG. 16 illustrates an embodiment of a tubular covering 120 partially divided into compartments 122. As shown, the tubular covering 120 includes a further portion 124 that may be divided into compartments. After subdivision into compartments 122, one or more compartments 122 may be removed from the tube 120 for implantation. Alternatively, in an embodiment wherein the tube is perforated into a plurality of compartments, the surgeon may select the number of compartments desired and cut along the applicable perforation. In some embodiments, some of the compartments may be prefilled with a substance for delivery and other compartments may be empty for filling by the surgeon. For example, ever other compartment between perforations may be preloaded or filled. The osteoimplant thus may be customized by filling the empty compartments with a desired substance.

For example, in some embodiments, a portion of the covering for example, one compartment of a multi-compartment covering, may be filled with autograft. Thus, the covering may be substantially empty prior to surgery. During surgery, a surgeon may remove autograft from the patient and place the autograft in the substantially empty compartment. Such placement may be done in any suitable manner. In one embodiment, the covering may be provided with a port for receiving an opening of an injection device and the autograft may be injected into the covering. Alternatively, the autograft may be mixed with allograft, synthetics, or any other desired substances or combination of substances.

Attachment mechanisms provided on the covering may be used to couple the covering to a site in vivo.

VI. Applications

The covering may be used in any suitable application. In some embodiments, the covering may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, e.g. edentulous patients), beneath trauma plates, tibial plateau defects, filling bone cysts, wound healing, around trauma, contouring (cosmetic/plastic/reconstructive surgery), and others. The delivery system may be used in a minimally invasive procedure via placement through a small incision, via delivery through a tube, or other. The size and shape may be designed with restrictions on delivery conditions.

An exemplary application for using a delivery system as disclosed is fusion of the spine. In clinical use, the covering and delivered substance may be used to bridge the gap between the transverse processes of adjacent or sequential vertebral bodies. The delivery system may be used to bridge two or more spinal motion segments. The covering surrounds the substance to be implanted, and contains the substance to provide a focus for healing activity in the body.

In other applications, the delivery system may be applied to transverse processes or spinous processes of vertebrae.

Generally, the delivery system may be applied to a pre-existing defect, to a created channel, or to a modified defect. Thus, for example, a channel may be formed in a bone, or a pre-existing defect may be cut to form a channel, for receipt of the delivery system. The covering may be configured to match the channel or defect. In some embodiments, the configuration of the covering may be chosen to match the channel. In other embodiments, the channel may be created, or the defect expanded or altered, to reflect a configuration of the covering. The covering may be placed in the defect or channel and, optionally, coupled using attachment mechanisms.

At the time just prior to when the delivery system is to be placed in a defect site, optional materials, e.g., autograft bone marrow aspirate, autograft bone, preparations of selected autograft cells, autograft cells containing genes encoding bone promoting action, etc., can be combined with the covering and/or with a substance provided within the covering. The osteoimplant can be implanted at the bone repair site, if desired, using any suitable affixation means, e.g., sutures, staples, bioadhesives, screws, pins, rivets, other fasteners and the like or it may be retained in place by the closing of the soft tissues around it.

U.S. Pat. No. 4,430,760 for Nonstress-bearing Implantable Bone Prosthesis, U.S. Pat. No. 6,740,093 for Method and Apparatus for Treating a Vertebral Body, U.S. Pat. No. 4,755,184 for Bone Augmentation Implant, U.S. Pat. No. 5,571,189 for Expandable Fabric Implant for Stabilizing the Spinal Motion Segment, U.S. Pat. No. 7,220,282 Annulus-Reinforcing Band, U.S. Pat. No. 7,208,015 for Bone Repair Device, and U.S. Patent Publication No. 2007/0073401 for Method for Repairing Bone disclose various fabrics and structures for containing materials for implanting in the body and are herein incorporated by reference in their entireties.

VII. Conclusion

In accordance with various embodiments, a delivery system for delivery a substance in vivo is provided. The delivery system comprises a covering and a substance. The covering may be a single or multi-compartment structure capable of at least partially retaining a substance provided therein until the covering is placed at a surgical site. Upon placement, the substance may be released (actively or passively) to the surgical site. The covering may participate in, control, or otherwise adjust, the release of the substance. The delivery system may be used to control availability of a substances provided within the delivery system to cells and tissues of a surgical site over time.

Although the invention has been described with reference to preferred embodiments, persons skilled in the art will recognize that changes may be made in form and detail without departing from the spirit and scope of the invention.

The invention claimed is:

1. A delivery system for delivering substances to a surgical site comprising:
a porous mesh covering comprising a biodegradable polymer, and a first compartment and a second compartment defined and formed from the mesh covering;
a first substance comprising fully demineralized bone fibers provided in the first compartment; and
a second substance comprising surface demineralized bone chips provided in the second compartment;
wherein the mesh covering retains the first substance and the second substance for placement at the surgical site and facilitates transfer of the first substance and the second substance or of surrounding materials, actively or passively through the mesh covering, upon implantation, wherein the second compartment is disposed adjacent to the first compartment, and the biodegradable polymer comprises at least one of poly(lactic acid) (PLA), poly(glycolic acid) (PGA), and poly(lactic-co-glycolic acid) (PLGA).

2. The delivery system of claim 1, wherein the first compartment and the second compartment are separated by a barrier.

3. The delivery system of claim 1, wherein the barrier is temporary.

4. The delivery system of claim 1, wherein the first compartment and the second compartment are in communication.

5. The delivery system of claim 1, wherein the mesh covering is perforated between the first compartment and the second compartment.

6. The delivery system of claim 1, wherein at least one of the first compartments and the second compartment is unfilled at manufacture.

7. The delivery system of claim 6, wherein the at least one unfilled first compartment or second compartment comprises a port for receiving a syringe.

8. The delivery system of claim 1, wherein the first compartment is formed of a first material and the second compartment is formed of a second material and wherein the first material and the second material are not the same.

9. The delivery system of claim 8, wherein the first material and the second material have different release characteristics.

10. The delivery system of claim 1, wherein the delivery system conforms to surrounding bony contours when implanted in vivo.

11. The delivery system of claim 1, wherein the delivery system provides a pathway for healing, cell penetration and tissue ingrowth.

12. The delivery system of claim 1, wherein the mesh covering further comprises a natural material.

13. The delivery system of claim 12, wherein the natural material is collagen.

14. The delivery system of claim 1, wherein the mesh covering comprises a synthetic material.

15. The delivery system of claim 14, wherein the synthetic material is a resorbable polymeric material.

16. The delivery system of claim 1, wherein the mesh covering is treated to have particles adhered thereto.

17. The delivery system of claim 16, wherein the particles are bone particles.

18. The delivery system of claim 1, wherein the mesh covering comprises a functional material.

19. The delivery system of claim 18, wherein the functional material is radiopaque.

20. The delivery system of claim 18, wherein the functional material is bacteriocidal.

21. The delivery system of claim 1, wherein the mesh covering further comprises a reinforcing material.

22. The delivery system of claim 1, wherein the mesh covering is flexible.

23. The delivery system of claim 1, wherein the first substance and the second substance are particulated and wherein the mesh covering retains particles of the first substance and the second substance in spatial proximity to one another.

24. The delivery system of claim 1, wherein the mesh covering comprises an actively releasing material and is configured to release such material during degradation of the mesh covering.

25. The delivery system of claim 1, wherein the mesh covering controls access to an interior of the delivery system by cells.

26. The delivery system of claim 1, wherein the delivery system expands in vivo.

27. The delivery system of claim 1, wherein the delivery system is generally tubular.

28. The delivery system of claim 1, further comprising a cage, wherein the mesh covering is placed in the cage.

29. The delivery system of claim 1, further comprising an attachment mechanism.

30. The delivery system of claim 29, wherein the attachment mechanism couples the first and second compartments.

31. The delivery system of claim 29, wherein the attachment mechanism attaches the delivery system to a tissue structure.

32. The delivery system of claim 1, wherein the first substance is homogenous.

33. The delivery system of claim 1, wherein the first substance is heterogeneous.

34. The delivery system of claim 1, wherein the bone is particulated.

35. The delivery system of claim 1, wherein the bone is enhanced demineralized bone matrix.

36. The delivery system of claim 1, wherein the first substance comprises a sequence of ingredients.

37. The delivery system of claim 1, wherein the first substance exhibits a gradient.

38. The delivery system of claim 37, wherein the gradient attracts cells along a pathway.

39. The delivery system of claim 1, wherein the first substance comprises a bioactive agent.

40. The delivery system of claim 1, wherein the first substance further comprises protein, carbohydrate, lipids, collagen, allograft bone, autograft bone, TCP, hydroxyapatite, growth factors, carriers for growth factors, growth factor extracts of tissues, demineralized bone matrix, bone marrow aspirate, concentrates of lipid derived or marrow derived adult stem cells, umbilical cord derived stem cells, committed or partially committed cells from the osteogenic or chondrogenic lineage, or combinations thereof.

41. The delivery system of claim 1, wherein the delivery system comprises a ring, a cage, a generally rectangular shape, a mesh, a suture-like wrap, a continuous tube, or a plurality of strings.

42. The delivery system of claim 1, wherein the delivery system is configured for healing vertebral compression fractures, minimally invasive procedures, posterolateral fusion, correction of adult or pediatric scoliosis, treating long bone defects, osteochondral defects, ridge augmentation, or wound healing.

43. The delivery system of claim 1, wherein the delivery system is adapted to bridge more than two spinal motion segments.

44. The delivery system of claim 1, wherein the delivery system is adapted to be applied to transverse processes or spinous processes of vertebrae.

45. The delivery system of claim 1, wherein the porous mesh covering comprising a biodegradable polymer has a pore size of about 100-200 µm.

* * * * *